(12) United States Patent
Ninomiya et al.

(10) Patent No.: US 7,059,103 B2
(45) Date of Patent: Jun. 13, 2006

(54) SEALING APPARATUS AND MANUFACTURING PROCESS OF SOFT ARTICLE HAVING SEALED PORTION

(75) Inventors: Akihide Ninomiya, Kagawa (JP); Hironori Nomura, Kagawa (JP); Junji Shinohara, Kagawa (JP); Hiroki Yamamoto, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/472,276

(22) PCT Filed: Mar. 20, 2002

(86) PCT No.: PCT/JP02/02691

§ 371 (c)(1),
(2), (4) Date: Sep. 17, 2003

(87) PCT Pub. No.: WO02/078935

PCT Pub. Date: Oct. 10, 2002

(65) Prior Publication Data
US 2004/0106506 A1    Jun. 3, 2004

(30) Foreign Application Priority Data
Mar. 28, 2001    (JP) .............................. 2001-091925

(51) Int. Cl.
B65B 9/06    (2006.01)

(52) U.S. Cl. ............................ 53/450; 53/455; 53/459; 53/477; 53/550; 53/555; 53/548; 156/73.1; 156/308.2; 156/580.1; 156/581; 493/205; 493/208

(58) Field of Classification Search .......... 53/550–555, 53/548, 561, 450, 455, 459, 477, 374.3, 374.5, 53/374.9; 156/64, 73.1, 308.2, 308.4, 580, 156/581, 580.1, 580.2; 493/205, 208
See application file for complete search history.

(56) References Cited

U.S. PATENT DOCUMENTS

| 4,614,078 | A | | 9/1986 | Kawabe |
| 4,758,293 | A | | 7/1988 | Samida |
| 5,588,944 | A | * | 12/1996 | Achelpohl et al. .......... 493/205 |
| 5,660,679 | A | * | 8/1997 | Rajala et al. ............. 156/580.1 |
| 5,667,608 | A | * | 9/1997 | Rajala et al. .............. 156/73.1 |
| 6,123,792 | A | * | 9/2000 | Samida et al. ............. 156/73.1 |

(Continued)

FOREIGN PATENT DOCUMENTS

JP    5-26005    6/1993

(Continued)

Primary Examiner—Stephen F. Gerrity
Assistant Examiner—Hemant M. Desai
(74) Attorney, Agent, or Firm—Darby & Darby

(57) ABSTRACT

Disclosed is a sealing apparatus wherein, as a drum (5) and a rotary base (6) are rotated together, a follower (10a) of a rocking support member (9) rockably provided on the outer periphery of the rotary base (6) is guided along a cam groove (15c) of a cam member (15) to drive the rocking support member (9) to rock. When the rotary drum (5) reaches a predetermined rotational position, an anvil (14) supported by the rocking support member (9) is urged onto a horn (8), and then, when it reaches another rotational position, the anvil (14) is moved away from the horn (8). Since the anvil (14) is driven by the rocking motion of the rocking support member (9), entire operation becomes quite simple, and a continuous soft work can be certainly clamped between the horn (8) and the anvil (14).

14 Claims, 14 Drawing Sheets

U.S. PATENT DOCUMENTS 6,309,487 B1 * 10/2001 Herrin et al. ............... 156/73.1
6,368,437 B1 * 4/2002 Ziegelhoffer et al. ...... 156/73.1
6,540,854 B1 * 4/2003 Couillard et al. ............. 156/64
6,634,539 B1 * 10/2003 Mlinar et al. ............ 228/110.1

FOREIGN PATENT DOCUMENTS

| JP | 6-27529 | 7/1994 |
|----|---------|--------|
| WO | WO-96/23645 A1 | 8/1996 |

* cited by examiner

SEALING APPARATUS AND MANUFACTURING PROCESS OF SOFT ARTICLE HAVING SEALED PORTION

This application is 371 of PCT/JP02/02691 filed on Mar. 20, 2002.

TECHNICAL FIELD

The present invention relates generally to a sealing apparatus for forming sealed portion in a continuous soft work for forming soft article, such as disposable diaper, sanitary napkin and so forth, and a manufacturing process of such soft article having sealed portion. More particularly, the invention relates to a sealing apparatus and a manufacturing process, which can certainly perform sealing operation with simple operation.

PRIOR ART

For example, Japanese Patent Application Laid-Open No. 10-513128 (PCT/US96/00618) discloses an apparatus for manufacturing soft article such as diaper, as non-individual body, by providing ultrasonic seal to a continuous web at regular intervals.

In the above-identified publication, an ultrasonic sealing mechanism constituted of a plurality of ultrasonic horns and anvils is provided in a rotary working drum for rotation together with the rotary working drum. The web is wrapped around the outer peripheral face of the rotary working drum to be fed from upstream side and downstream side by rotation of the rotary working drum. The ultrasonic horn is driven by a cam for reciprocation in width direction on the outer peripheral face of the rotary working drum. Within the rotary working drum, the anvils are provided in opposition to the ultrasonic horns. Then, while the continuous web is fed by rotation of the rotary working drum, the ultrasonic horn is moved transversely in the width direction on the web for a given distance for forming line form ultrasonic sealed portions in the web.

However, in the sealing apparatus disclosed in Japanese Patent Application Laid-Open No. 10-513128, the operation of reciprocal motion of the ultrasonic horn in the width direction on the outer peripheral face of the rotary working drum, is performed by cam action. Therefore, reciprocating speed of the ultrasonic horn is required to be varied according to variation of rotation speed of the drum. Accordingly, moving speed of the ultrasonic horn is varied depending upon production speed to vary a time among a pressure and the time as sealing conditions to make it difficult to achieve good seal. Namely, in the sealing apparatus disclosed in the above-identified publication, since cam shape and drum diameter are limited, only production speed corresponding thereto can be achieved. Accordingly, when the production speed is to be varied after production of the sealing apparatus, an allowable range for varying the production speed is structurally quite limited.

On the other hand, upon continuously sealing absorbent article, such as diaper, it is typical that rubber or gather provided in the web is to be subject to the ultrasonic seal together with the web. In case of the product having the rubber or gather, undulation is formed in the web. When sealing operation for such web is performed by means of the sealing apparatus disclosed in Japanese Patent Application Laid-Open No. 10-513128, the reciprocating ultrasonic horn is moved up and down depending upon the undulation to possibly cause variation of pressure to be applied to the web. Therefore, difficulty is encountered in achieving uniform ultrasonic seal in the web. This can result in fluctuation of finishing and/or strength of the sealed portion.

Furthermore, it requires complicate control of an air cylinder so as to control the air cylinder to apply a pressurizing force to the ultrasonic horn when the ultrasonic horn comes into contact with the web, and to control the air cylinder to release the pressurizing force on the ultrasonic horn when the ultrasonic horn is moved away from the web.

Also, upon sealing the web for producing the absorbent article, the thickness of the web tends to be different in the portions to be sealed. In this case, when the ultrasonic horn and the anvil are pressurized by a single pressurizing means, the portion of the web having larger thickness is given greater pressurizing force than that given to the portion of the web having smaller thickness so that welding is dominantly progressed in the larger thickness portion in comparison with the smaller thickness portion. Therefore, the web in the larger thickness portion becomes stiff to differentiate sealing strength and taste of finishing in the sealed portion.

DISCLOSURE OF THE INVENTION

The present invention has been worked out in view of the foregoing shortcomings in the prior art. It is therefore an object of the present invention to provide a sealing apparatus and a manufacturing process of soft article having sealed portion superior in manufacturing ability in simple construction and achieving uniform seal.

Another object of the present invention is to provide a sealing apparatus and a manufacturing process of soft article having sealed portion, which can uniformly weld a portion to be sealed in a soft work having locally different thicknesses and prevent occurrence of portions having difference in the sealing strength and taste of finishing.

According to a first aspect of the present invention, there is provided a sealing apparatus for forming sealed portions in a soft work continuously fed thereto, the sealing apparatus comprising: a rotating portion; rotating driving means for driving the rotating portion to rotate; and a plurality of sealing mechanisms arranged along a rotating direction of the rotating portion to move along with the rotating portion, each sealing mechanism including a first clamping member and a second clamping member for clamping the soft work therebetween within a predetermined angular range with respect to a rotation center of the rotating portion for forming the sealed portions in the soft work, wherein in each sealing mechanism, the first clamping member is located on the side of the rotation center of the rotating portion to orient a seal opposing surface thereof outwardly in a normal direction extending from the rotation center, the second clamping member corresponding to the first clamping member is located outside of the first clamping member in the normal direction, and the second clamping member is pivotably supported on the rotating portion for pivoting between a claming position, in which a seal opposing surface thereof is urged toward the seal opposing surface of the first clamping member, and a retracted position located away from the first clamping member, and wherein rocking driving means is provided for driving the second clamping member to pivot as the rotating portion rotates so that the second clamping member is located in the clamping position within the predetermined angular range and located in the retracted position within another angular range so as not to interfere with feeding of the soft work into the sealing mechanisms and ejecting of the soft work from the sealing mechanisms.

With the construction of the first aspect of the invention as set forth above, the second clamping member forming the sealing mechanism can be radially pivoted away from the radially arranged first clamping member to be placed in the retracted position. Therefore, the second clamping member can be moved between the clamping position for performing sealing operation and the retracted position not interfering with transportation of the continuous soft work only by simple rocking or pivoting motion. Also, since sealing operation is performed by contacting and releasing the first clamping member and the second clamping member, sealing operation can be performed at high speed.

For example, the continuous soft work includes at least a sheet which can be fusion-bonded. The continuous soft work may further include liquid absorptive bodies spaced apart from each other in a feeding direction thereof and supported by the sheet, and sealing may be effected in a condition where each liquid absorptive body is located between adjacent sealing mechanisms and the sheet is folded back.

By positioning the liquid absorptive body between adjacent sealing mechanisms, the sheet can be certainly sealed at the portion where the liquid absorptive body is not present.

Preferably, the rotating portion includes a rotary drum, and the first clamping member is arranged inside of the rotary drum so that the seal opposing surface of the first clamping member is located at a position projecting from an outer peripheral face of the rotary drum.

With this construction, the folded sheet can be certainly sealed in the condition where the liquid absorptive body is located between adjacent sealing mechanisms and on the outer peripheral face of the rotary drum.

Preferably, the seal opposing surface of the second clamping member as pivoted to the retracted position is pivoted over about 90° with respect to a rotation center axis of the rotating portion.

By pivoting the second clamping member over the foregoing angle to the retracted position, the second clamping member can be certainly retracted to the position not interfering with transportation (feeding and ejecting) of the continuous soft work.

For example, the rocking driving means is formed from a cam profile fixed at a position opposing to the rotating portion and a follower to move along the cam profile as the rotating portion rotates for pivoting the second clamping member between the clamping position and the retracted position.

In this case, the cam profile may be defined by a continuous cam groove extending to surround the rotation center of the rotating portion but spaced away from the rotation center.

For example, the follower is mounted on a rocking support member supporting the second clamping member so that the rocking support member is pivoted between the clamping position and the retracted position by movement of the follower along the cam profile. In an alternative, there may be provided a rocking support member supporting the second clamping member and a link mechanism provided between the rocking support member and the follower so that the rocking support member is pivoted between the clamping position and the retracted position via the link mechanism by movement of the follower along the cam profile.

As set forth above, by providing fixed cam profile and pivotally driving the second clamping member with taking rotating motion of the rotating portion as driving power source, it becomes unnecessary to provide another driving power source, such as cylinder mechanism or the like, for pivoting the second clamping member per the sealing mechanism.

In the first aspect of the invention, it is also preferred that the rotating portion includes a rocking support member pivotably supported by a rocking shaft, and the second clamping member is supported on the rocking support member via an elastic member so that when the second clamping member is pivoted to the clamping position, the second clamping member is biased toward the first clamping member by an elastic force developed by the elastic member.

By biasing the second clamping member toward the first clamping member via the elastic member, uniform pressure can be easily applied to respective portions of the soft work with the seal opposing surface of the second clamping member and the seal opposing surface of the first clamping member even when the soft work has a structure having unevenness.

According to a second aspect of the present invention, there is provided a sealing apparatus comprising: a sealing mechanism having a first clamping member and a second clamping member for clamping a fusion-bondable soft work there between for forming sealed portions in the soft work; and driving means for driving the second clamping member to clamp the soft work between the first clamping member and the second claming member and to move away from the first clamping member, wherein the second clamping member is supported on a supporting member via an elastic member and the supporting member is driven by the driving means so that the second member is biased toward the first clamping member by an elastic force developed by the elastic member, and the elastic member has a deformable casing into which fluid is introduced.

In the foregoing second aspect of the invention, since the elastic member having the casing (e.g., bag shaped casing) into which fluid is introduced, is employed, the second clamping member can be biased to follow unevenness of the soft work or difference of thickness of the soft work, so that such soft work can be clamped between the first clamping member and the second clamping member as uniformly as possible. As a result, quality of sealed portion can be improved.

For example, the soft work is continuously fed to the sealing apparatus and a plurality of sealing mechanisms are arranged at intervals along a feeding direction of the continuous soft work so that the sealed portions are formed in the continuous soft work at intervals along the feeding direction by means of the sealing mechanisms.

Preferably, the sealing apparatus further comprises a rotating portion, and a plurality of sealing mechanisms are arranged at intervals along a rotating direction of the rotating portion and the soft work is continuously fed to the rotating portion so that, as the rotating portion rotates, the sealed portions are formed in sequential order by means of the sealing mechanisms.

For example, the continuous soft work includes a sheet which can be fusion-bonded and liquid absorptive bodies spaced apart from each other in a feeding direction thereof and supported by the sheet, and sealing is effected in a condition where each liquid absorptive body is located between adjacent sealing mechanisms and the sheet is folded back.

Here, it is preferred that the sealing apparatus further comprises pressure setting means for varying pressure of fluid within the casing.

By providing the pressure setting means, the pressure in the casing can be set at an optimal value depending upon kind of the soft work. Therefore, the soft work can be clamped between the second clamping member and the first clamping member under an optimal pressure.

Preferably, a plurality of elastic members for supporting the second clamping member are provided in the supporting member. In this case, more preferably, the sealing apparatus further comprises pressure setting means for individually setting pressure of fluid within respective casing of the plurality of elastic members.

By biasing the second clamping member with the plurality of elastic members, the soft work having uneven profile or having portions of different thicknesses can be clamped with a uniform clamping force between the second clamping member and the first clamping member.

For example, the sealing mechanism is an ultrasonic sealing device, and one of the first clamping member and the second clamping member is a horn and the other is an anvil.

However, it is, of course, possible to perform heat sealing with the first clamping member and the second clamping member of the sealing mechanism.

According to a third aspect of the present invention, there is provided a method for manufacturing soft articles respectively having sealed portions, comprising:

forming sealed portions in a continuous soft work by clamping the soft work between a first clamping member and a second clamping member, the first clamping member and the second clamping member forming a sealing mechanism; and cutting the soft work before, simultaneously with or after the forming step, wherein the second clamping member is biased toward the first claming member via an elastic member and the elastic member has a deformable casing into which fluid is introduced.

In the soft articles, such as disposable diaper, sanitary napkin and so forth produced by the foregoing manufacturing method, material of the soft work, such as sheet and so forth, can be uniformly fusion-bonded in the portion to be sealed, to thereby improve quality of the sealed portion.

In the third aspect of the invention, for example, a plurality of sealing mechanisms are arranged at intervals along a feeding direction of the continuous soft work so that the sealed portions are formed in the continuous soft work at intervals along the feeding direction by means of the sealing mechanisms. Preferably, a plurality of sealing mechanisms are arranged at intervals along a rotating direction of a rotating portion and the continuous soft work is fed to the rotating portion so that, as the rotating portion rotates, the sealed portions are formed in sequential order by means of the sealing mechanisms.

For example, with fluid pressure in the casing being set at a predetermined value, optimal sealing condition can be set depending upon structure and/or thickness of the soft work.

More preferably, a plurality of elastic members are provided and respective elastic members bias the second clamping member. In this case, it is preferred that internal pressures of the plurality of elastic members are set independently.

By independently setting the internal pressures as set forth above, uniform fusion-bonding quality can be obtained even when the continuous soft work has portions having different thicknesses in a region where the sealed portions are to be formed.

For example, in case where the continuous soft work has portions having different thickness in a region where the sealed portions are to be formed, it is preferred that internal fluid pressure of the elastic member biasing the second clamping member toward a portion having larger thickness in the soft work and internal fluid pressure of the elastic member biasing the second clamping member toward a portion having smaller thickness in the soft work are set independent of each other.

Here, the continuous soft work may include a sheet which can be fusion-bonded and liquid absorptive bodies spaced apart from each other in a feeding direction thereof and supported by the sheet, and sealing may be effected at positions between adjacent liquid absorptive bodies in a condition where the sheet is folded back.

For example, in order to make the quality of the sealed portion uniform, it is preferred that the set pressure of the fluid in the elastic member for applying the biasing force to the portion having smaller thickness is set higher than the set pressure of the fluid in the elastic member for applying the biasing force to the portion having larger thickness.

In the third aspect of the invention, too, the sealing mechanism may be an ultrasonic sealing device, and one of the first clamping member and the second clamping member may be a horn and the other may be an anvil.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

BEST MODE FOR IMPLEMENTING THE INVENTION

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
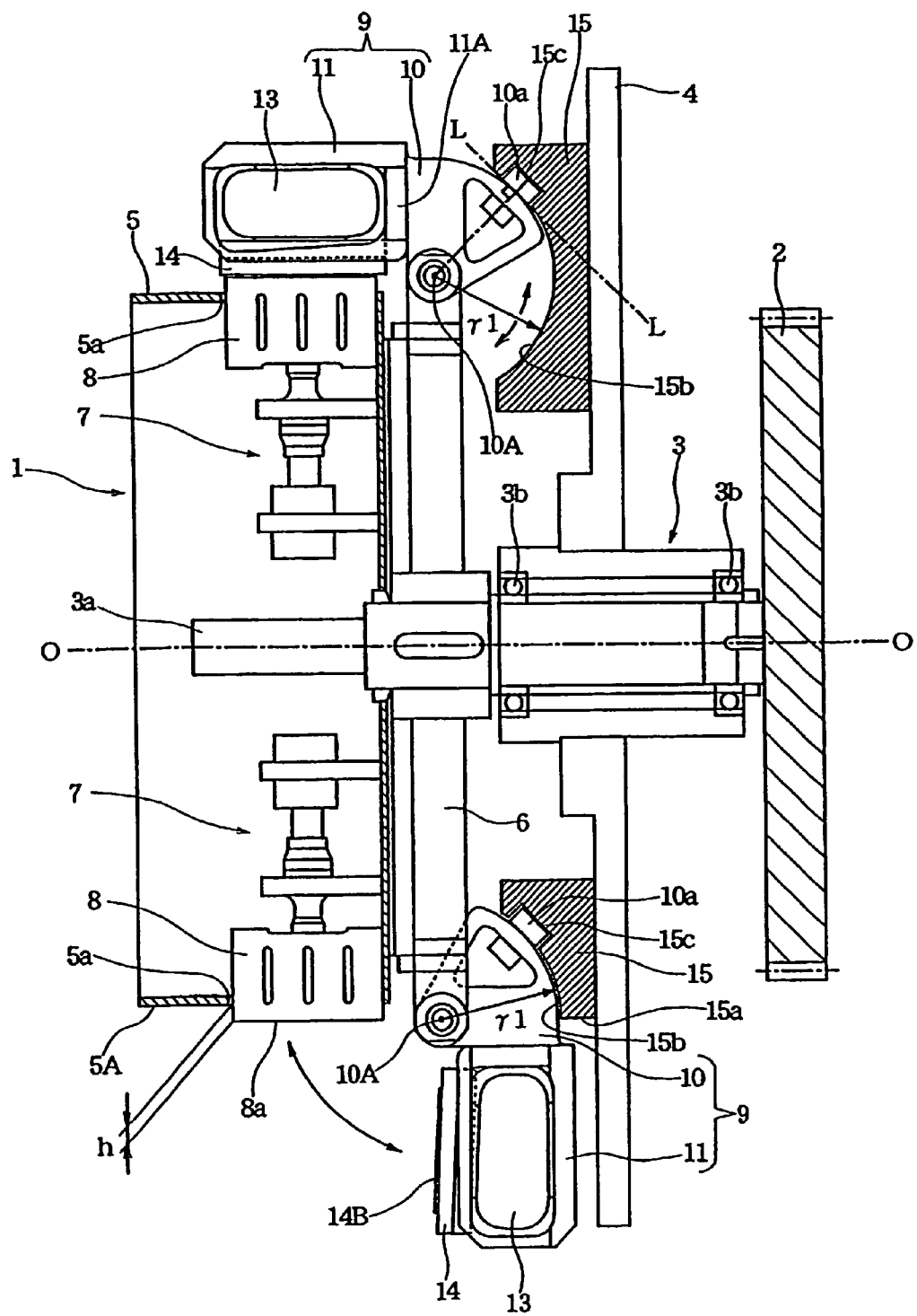
FIG. 1 is a section of a sealing apparatus according to a first embodiment of the present invention as taken along line I—I of FIG. 3.
Figure 2:
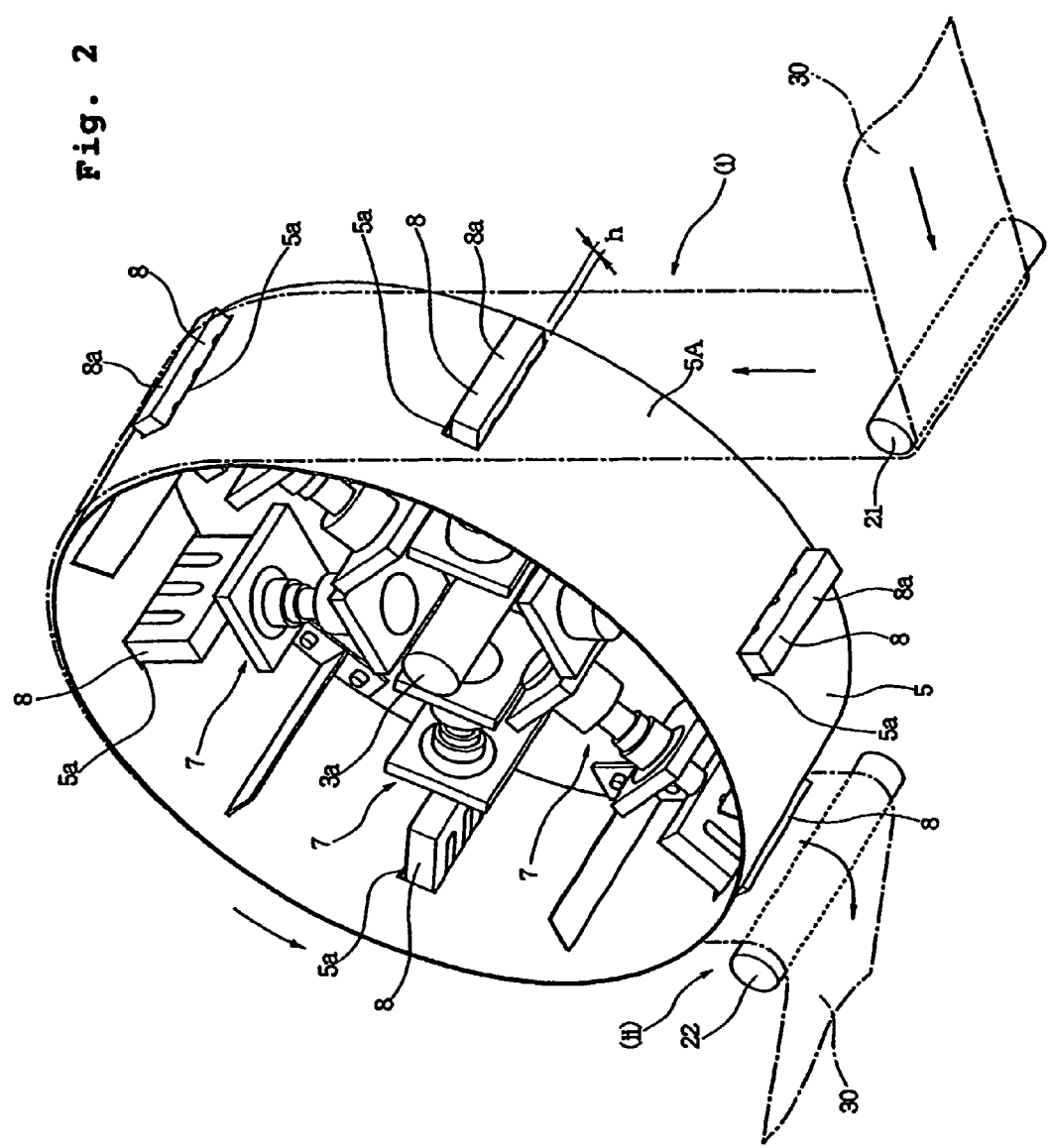
FIG. 2 is a perspective view for explaining a rotating portion of the sealing apparatus.
Figure 3:
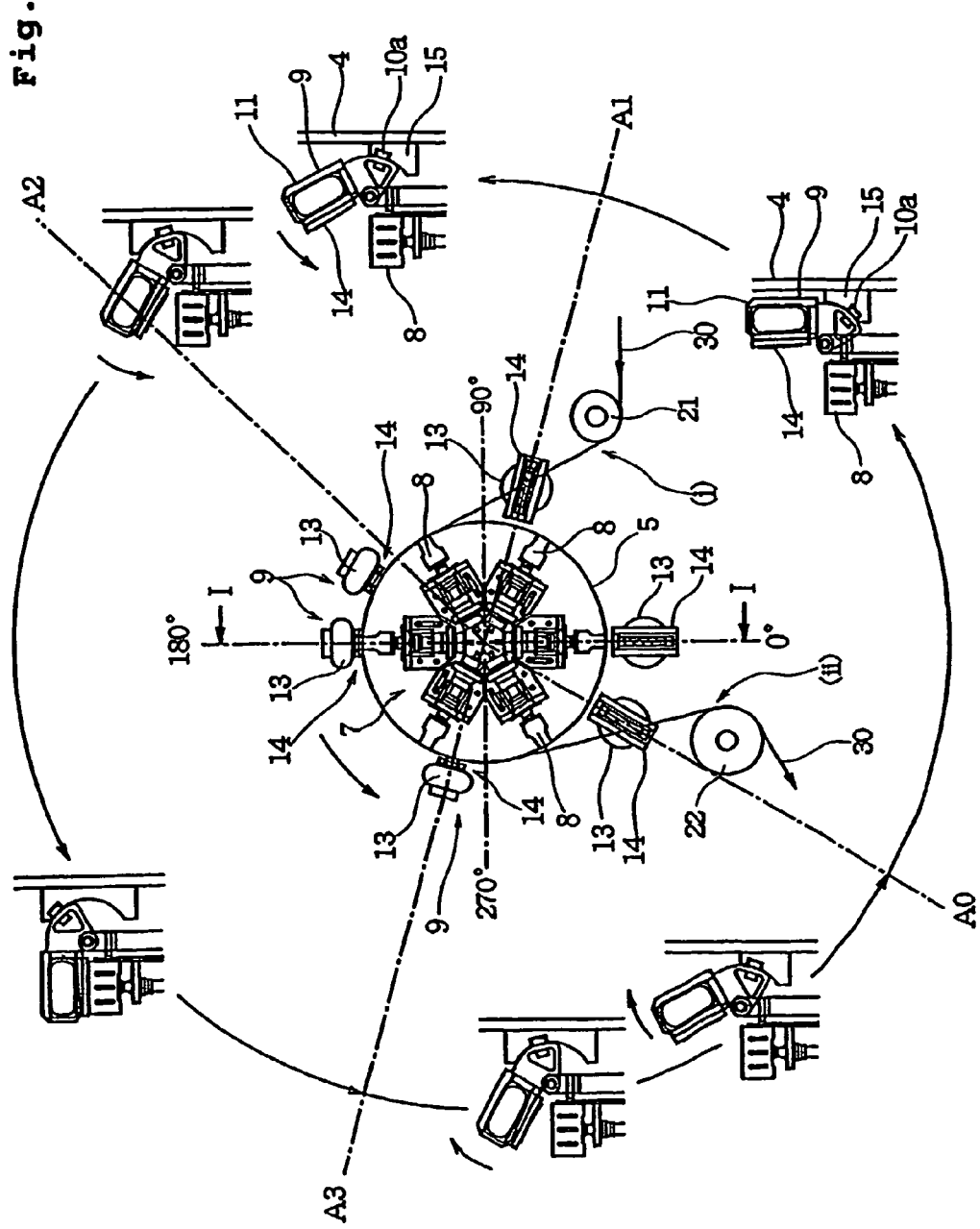
FIG. 3 is an explanatory illustration showing operating condition of the sealing apparatus.
Figure 4:
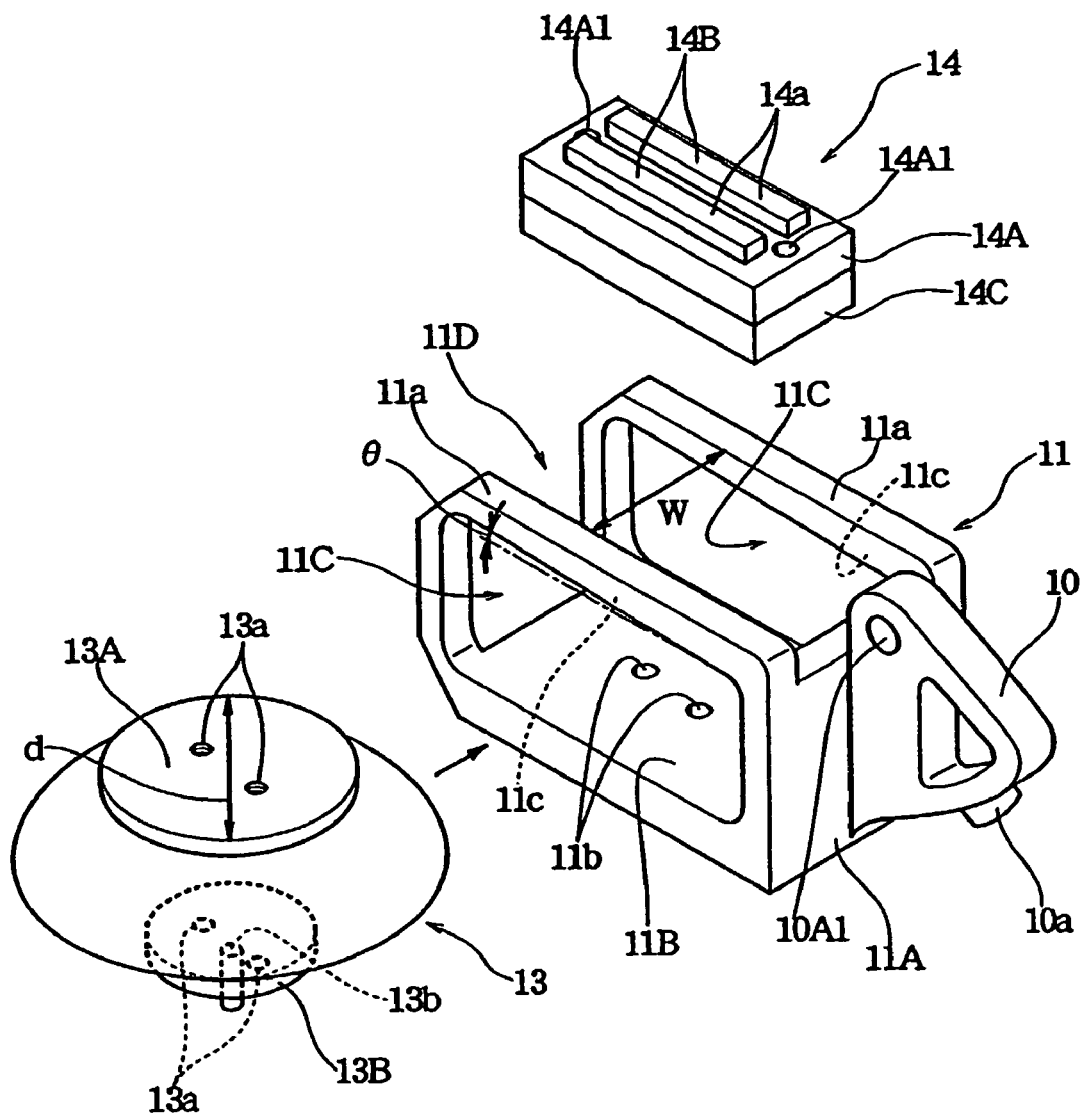
FIG. 4 is an exploded perspective view showing a structure of a rocking support member.
Figure 5:
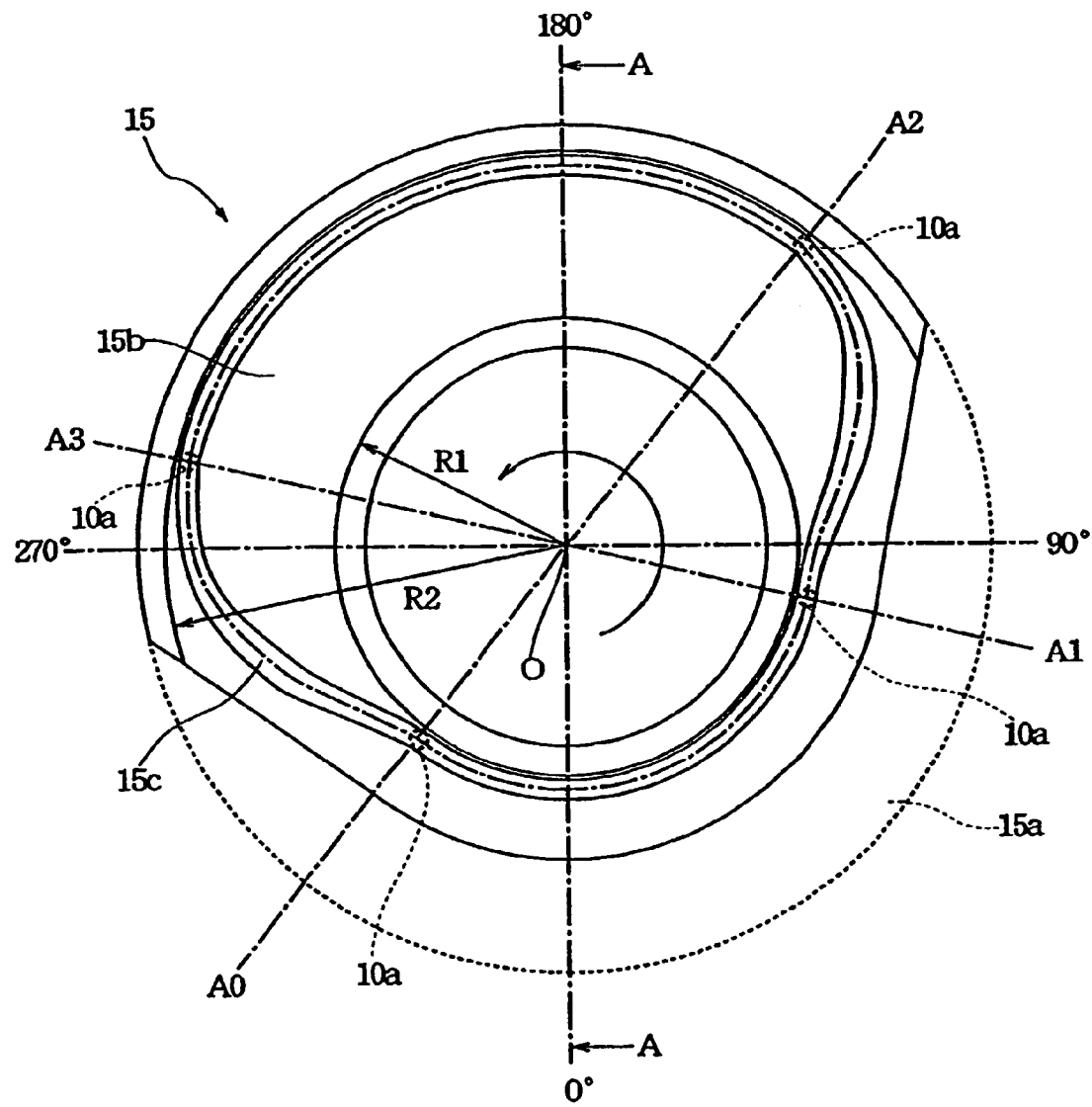
FIG. 5 is a front elevation showing a shape of a cam member on the side of a stationary portion.
Figure 6:
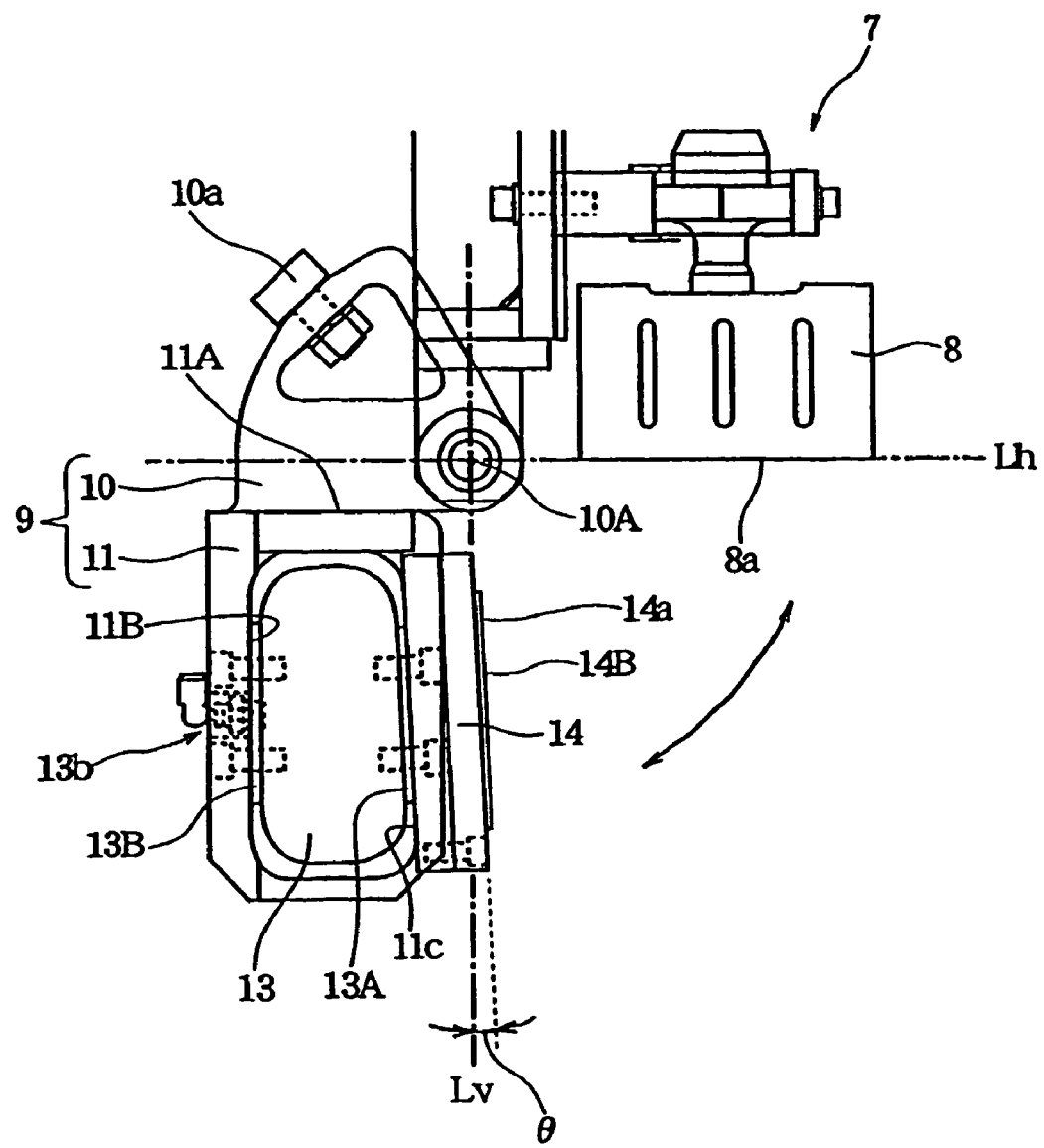
FIG. 6 is a side elevation showing a condition where an anvil is moved at a retracted position away from a horn.
Figure 7A:
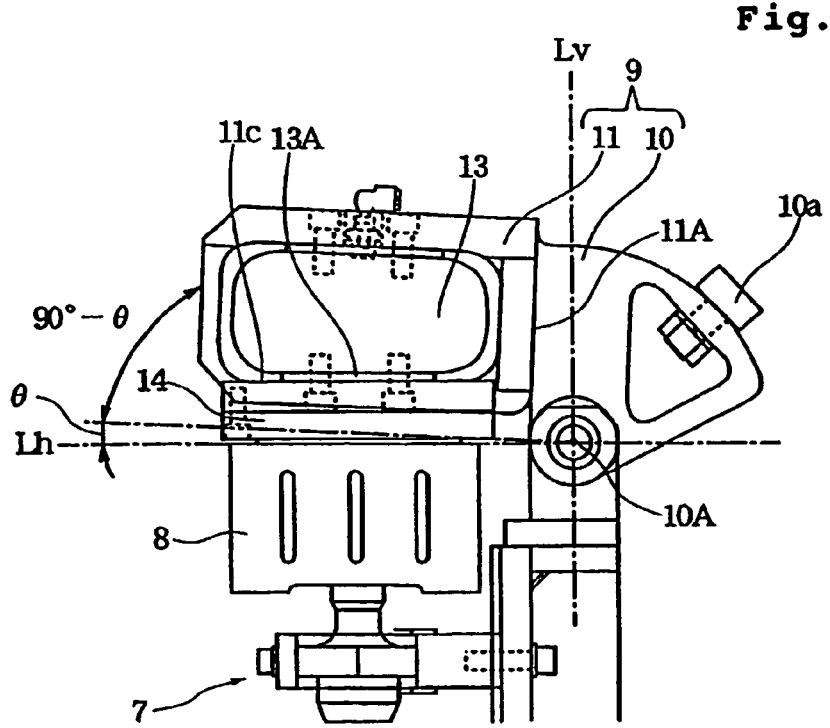
FIG. 7A is a side elevation showing a condition where the rocking support member is pivoted to contact the anvil to the horn.
Figure 7B:
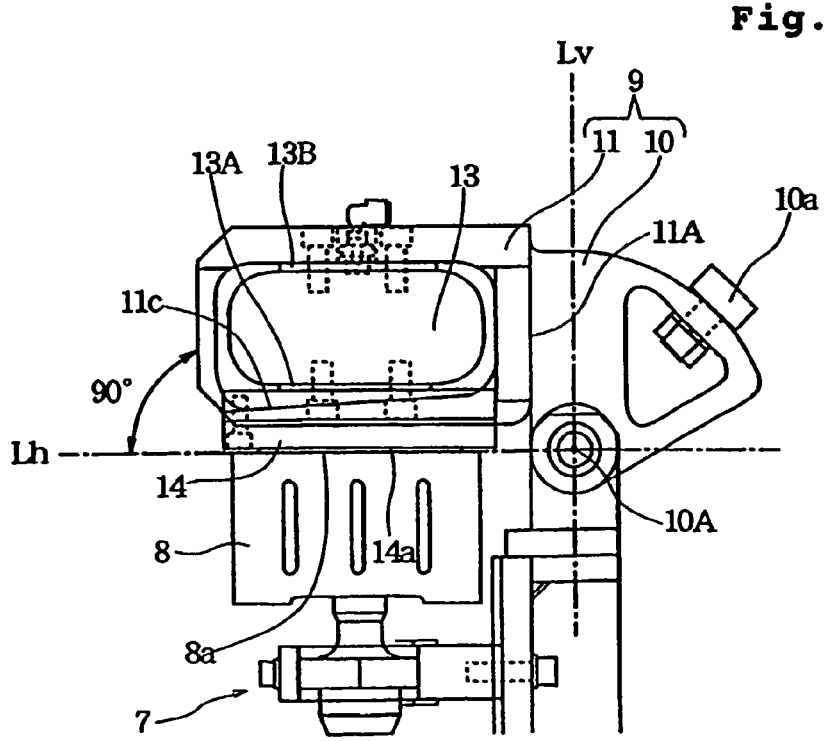
FIG. 7B is a side elevation showing a condition where the anvil is urged to the horn under pressure with compressing an elastic member.

FIG. 1 is a vertical section of a sealing apparatus according to a first embodiment of the present invention as taken along line I—I of FIG. 3, FIG. 2 is a perspective view for explaining a rotating portion of the sealing apparatus, FIG. 3 is an explanatory illustration showing operating condition of the sealing apparatus, FIG. 4 is an exploded perspective view showing a structure of a rocking support member, FIG. 5 is a front elevation showing a shape of a cam member on the side of a stationary portion, FIG. 6 is a side elevation showing a condition where an anvil (second clamping member) is moved at a retracted position away from a horn (first clamping member), FIG. 7A is a side elevation showing a condition where the rocking support member is pivoted to contact the anvil to the horn, and FIG. 7B is a side elevation showing a condition where the anvil is urged onto the horn under pressure with compressing an elastic member.

In a sealing apparatus 1 shown in FIG. 1, a bearing portion 3 is provided on a stationary table 4 as stationary portion. A rotary shaft 3a is rotatably supported by ball bearings 3b held in the bearing portion 3. In FIG. 1, a rotation center axis of the rotary shaft 3a is shown by O—O. On a base end portion of the rotary shaft 3a on right side in the drawing, a timing wheel 2 having teeth on the circumference is fixed. On the timing wheel 2, a cogged belt is wrapped around. The cogged belt is driven by a driving force from a driving source having a not shown motor for applying the driving force to the timing wheel 2. Then, the rotary shaft 3a is continuously driven to rotate at a constant angular velocity in counterclockwise direction in the condition as viewed from left side of FIG. 1. In the shown embodiment, rotating driving means is formed from the driving source, the cogged belt and the timing wheel 2.

On the rotary shaft 3a, a rotary base 6 to be a rotating portion is rigidly secured. On the rotary base 6, a rotary drum 5 is secured. The rotary base 6 is placed in opposition with the stationary table 4 in parallel relationship.

As shown in FIGS. 1 and 2, on the outer peripheral face 5A of the rotary drum 5, a plurality of rectangular windows 5a elongated in the direction parallel to the rotation center axis O—O are formed. The rectangular windows 5a are arranged at an equal pitch in circumferential direction. In the shown embodiment, the windows 5a are arranged in six angular positions 60° apart from each other with respect to the rotation center axis O—O.

The rotating portion is provided with a sealing mechanism. This sealing mechanism has first and second clamping members for clamping and sealing a continuous soft work therebetween. In the shown embodiment, the sealing mechanism is an ultrasonic sealing mechanism, of which the first clamping member is a horn 8 and the second clamping member is an anvil 14.

The horns 8 and the anvils 14 are both provided on the rotating portion for rotation together with the rotary base 6 and the rotary drum 5. The horns 8 are secured on the rotary base 6 within the rotary drum 5. The horns 8 and ultrasonic generating means 7 connected to the horns are arranged radially about the rotation center axis O—O. Here, the angular positions of the horns 8 and the ultrasonic generating means 7 match the angular positions of the windows 5a. Respective horns 8 are externally projected through the windows 5a of the rotary drum 5 to have seal opposing surfaces 8a at the leading ends thereof. The seal opposing surfaces 8a of the horns 8 are oriented outwardly in normal direction (radial direction) about the rotation center axis O—O and located parallel to the rotation center axis O—O. Projecting height of each of the seal opposing surfaces 8a from the outer peripheral face of the rotary drum 5 is h.

The rotary base 6 is of hexagonal shape. Rocking support members 9 are provided on the outer periphery portion of the rotary base 6. Each rocking support member 9 is constructed to include a rocking portion 10 and a holding portion 11. The rocking portion 10 and the holding portion 11 are fixed with each other. The rocking portion 10 is formed into substantially fan shaped configuration. By a rocking shaft 10A provided at the center of curvature of the fan shape, the rocking portion 10 is pivotably supported with respect to the outer periphery portion of the rotary base 6. The rocking shaft 10A is oriented perpendicular to the rotation center axis O—O. Thus, the rocking support member 9 is pivotable about the rocking shaft 10A between clamping position and retracted position.

A cam member 15 is rigidly secured on the surface of the stationary table 4 in opposition to the rotary base 6. As shown in FIG. 5, when viewed from the front side, the cam member 15 is of partly cut-out disc shape. The cut-out portion is indicated at 15a.

The center of the cam member 15 matches with the rotation center axis O—O of the rotating portion. On the surface of the cam member 15, a groove portion 15b is formed between an inner radius R1 and an outer radius R2 about the rotation center axis O—O. As shown in FIG. 1, a cross-sectional shape of the groove portion 15b is arc-shape of radius r1 about a pivoting center of the rocking portion 10 (center of the rocking shaft 10A). As shown in FIG. 5, a concave surface of the groove portion 15b is of doughnut shape extending entire circumference about the rotation center axis O—O. As shown in lower part of FIG. 1, in the cut-out portion 15a of the cam member 15, the outer periphery side of the groove portion 15b is cut out.

On the concave surface of the groove portion 15b, a cam groove 15c to be a cam profile is formed. As shown in FIG. 1, the cam groove 15c is recessed in a direction perpendicular to a tangential line L—L of the curve of the concave surface of the groove portion 15b (oriented in radial direction with respect to the axial center of the rocking shaft 10A). On the circumferential edge of the rocking portion 10, a follower 10a is provided. The follower 10a is a rotatable roller. In the alternative, the follower 10a may be a non-rotatable projection. When the rotary base 6 is driven to rotate, the follower 10a is moved along the cam groove 15c. In the shown embodiment, the cam member 15 and the follower 10a form rocking driving means for rocking the rocking support member 9.

As shown in FIG. 5, the cam groove 15c extends along an arc of constant radius about the rotation center axis O—O at a position the most distant from the rotation center axis O—O within an angular range between angular positions A2 and A3, and also extends along an arc of constant radius about the rotation center axis O—O at a position the closest to the rotation center axis O—O within an angular range between angular positions A0 to A1.

Accordingly, while the follower 10a moves from the angular position A1 to the angular position A2, the rocking support member 9 is pivoted toward the outer peripheral face 5A of the rotary drum 5 to reach the clamping position, and while the follower 10a moves from the angular position A2 to the angular position A3, the rocking support member 9 is maintained in the clamping position, as shown in upper portion of FIG. 1. On the other hand, while the follower 10a moves from the angular position A3 to the angular position A0, the rocking support member 9 is pivoted toward the stationary table 4 about 90° to reach the retracted position, and while the follower 10a moves from the angular position A0 to the angular position A1, the rocking support member 9 is maintained in the retracted position, as shown in lower portion of FIG. 1.

FIG. 4 shows the holding portion 11 as viewed from the side opposed to the rotary drum 5. Within the holding portion 11, an elastic member 13 is mounted. On the elastic member 13, the anvil 14 as the second clamping member of the sealing mechanism is supported.

As shown in FIG. 4, the holding portion 11 comprises: a rear side portion having a fixing surface 11A, on which the rocking portion 10 is secured; a bottom side portion having a mounting surface 11B, on which the elastic member 13 is secured; and two frame portions 11a and 11a on 1 ft and right sides thereof. In the holding portion 11, therefore, openings 11C and 11C are formed on the left and right sides, and an opening 11D is formed between the two frame portions 11a and 11a to be opposed to the rotary drum 5. As shown in FIG. 4, the rocking portion 10 has a supporting hole 10A1 to receive the rocking shaft 10A for pivotably supporting the rocking portion 10.

The elastic member 13 has: a flexibly and elastically deformable bag shaped body (casing); a disc-shaped supporting plate 13A mounted on the top of the bag shaped body; and a disc-shaped fixing plate 13B mounted on the bottom of the bag shaped body. The bag body of the elastic member 13 is made of an elastically deformable material, such as rubber, or a composite material, such as rubber combined with reinforcing member. By supplying an air as working fluid into a hollow portion of the bag body, the bag body functions as air damper or air spring. Here, the internal pressure of the bag body is set at a predetermined value by the supplied air pressure.

Both the supporting plate 13A and the fixing plate 13B are provided with vertically extending tap holes 13a. The fixing plate 13B is further provided with a nozzle 13b, to which an air pipe is connected. The internal pressure of the elastic member 13 can be set by air pressure introduced through the air pipe and the nozzle 13b. Means for setting internal pressure of the elastic member 13 has a construction comparable with that discussed later with respect to another embodiment with reference to FIG. 14. Specifically, the air pressure to be supplied to each of the elastic members 13 provided in a plurality of sealing mechanisms can be set independently of the other.

The elastic member 13 is installed in the holding portion 11 in such a state that its radially expanded portions protrude outwardly through the openings 11C and 11C. The tap holes 13a and 13a formed in the fixing plate 13B are placed in alignment with mounting holes 11b and 11b formed in the mounting surface 11B of the holding portion 11 for receiving not shown fastening bolts which are inserted and tightened from outside of the holding portion 11. Thus, the elastic member 13 is fixed in the holding portion 11.

A diameter d of the supporting plate 13A of the elastic member 13 is set to be greater than a width dimension W of the opening 11D. When the elastic member 13 is fixed in the holding portion 11, therefore, the supporting plate 13A is brought opposite inner surfaces 11c and 11c of the frame portions 11a and 11a. Accordingly, when the elastic member 13 is in expanded condition, the surface of the supporting plate 13A is urged onto the inner surfaces 11c and 11c under pressure.

Here, the inner surfaces 11c and 11c of the frame portions 11a and 11a are not parallel to the mounting surface 11B but are tilted at an angle θ such that the inner surfaces 11c and 11c go away from the mounting surface 11B as they go away from the rocking portion 10. It should be noted that the fixing surface 11A on which the rocking portion 10 is fixed, is at 90° with respect to the mounting surface 11B.

Therefore, when the elastic member 13 is expanded within the holding portion 11 to urge the surface of the supporting plate 13A into contact with the inner surfaces 11c and 11c of the frame portions 11a and 11a under pressure, the surface of the supporting plate 13A is not in parallel relationship with the mounting surface 11B but tilted at the tilting angle θ to increase distance to the mounting surface 11B as increasing distance from the rocking portion 10.

The anvil 14 has a base 14A with a uniform thickness over its entire length, and a pair of ridge portions 14B and 14B formed on the surface of the base 14A to extend in the longitudinal direction in parallel relationship with each other. Surfaces of the ridge portions 14B and 14B serve as seal opposing surfaces 14a and 14a to be opposed to the horn 8. The seal opposing surfaces 14a and 14a serve as pattering surfaces for defining a pattern of sealed portions to be formed in the continuous soft work.

The base 14A of the anvil 14 is provided at its longitudinally opposed two ends with through holes 14A1 and 14A1, and mounted on a support base 14C by means of not shown bolts. Furthermore, the support base 14C has not shown through holes formed at two positions. By fastening with not shown bolts inserted into the tap holes 13a and 13a and into the through holes formed in the support base 14C, the base 14A and the support base 14C are firmly secured on the surface of the supporting plate 13A.

The support base 14C of the anvil 14 and the seal opposing surfaces 14a are parallel with each other. Therefore, in the condition where the anvil 14 is fixed on the supporting plate 13A of the elastic member 13 within the holding portion 11, the seal opposing surfaces 14a are tilted at the tilting angle θ to increase distance to the mounting surface 11B as increasing distance from the rocking portion 10 (rocking shaft 10A).

Next, discussion will be given for one example of a continuous soft work 30 to be supplied to the sealing apparatus 1 with reference to FIGS. 8A and 8B. The soft work 30 is supplied to the sealing apparatus 1 in folded condition as shown in FIG. 8B. FIG. 9 is a section taken along line IX—IX of FIG. 8B and showing a condition where the sealed portion is formed, and FIG. 10 is a section taken along line X—X of FIGS. 8B and 9.

FIG. 8B shows the continuous soft work 30 in which sealed portions S has been formed with the horns 8 and the anvils 14 of the sealing apparatus 1. After forming the sealed portions S in the continuous soft work 30, the continuous soft work 30 is cut along cutting lines C1—C1 between adjacent sealed portions S to manufacture the pants type disposable diapers as soft absorbent articles. On the other hand, FIG. 8A show the continuous soft work 30 in developed condition.

Figure 8A:
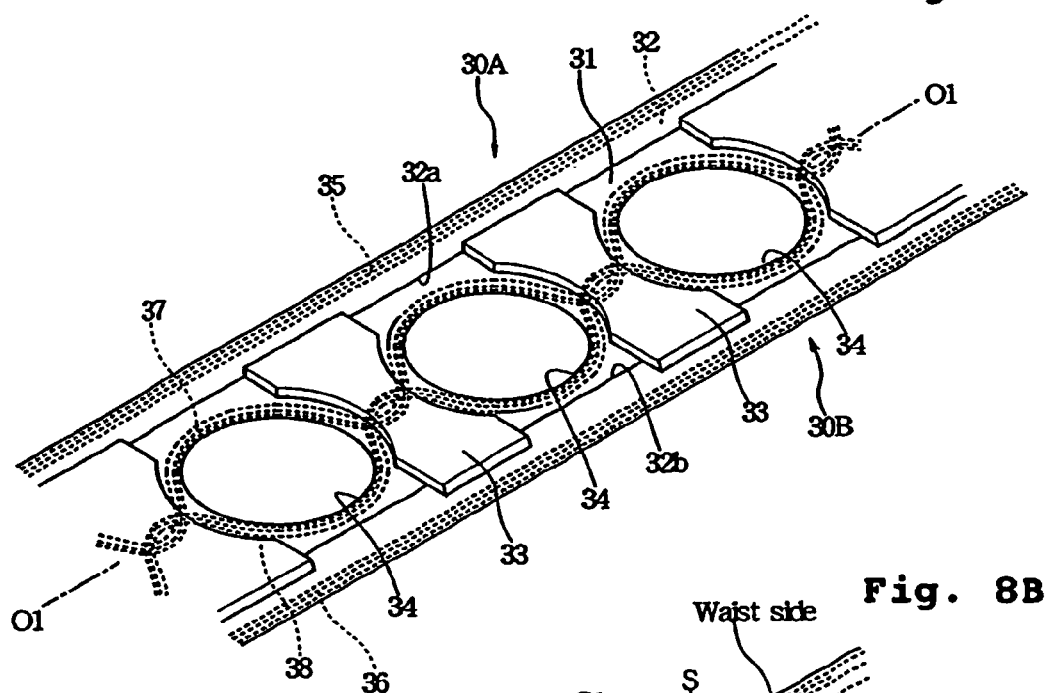
FIG. 8A is a perspective view showing a developed condition of a continuous soft work.
Figure 8B:
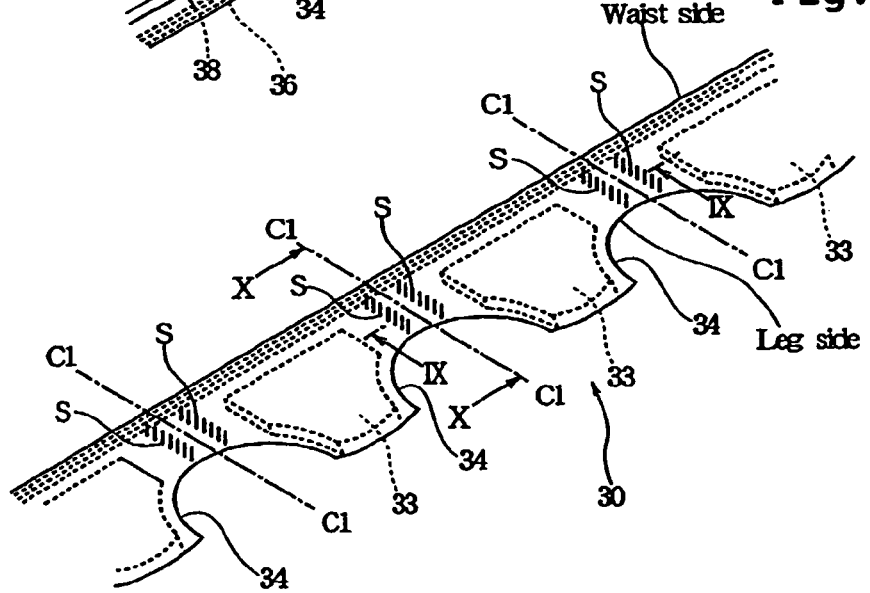
FIG. 8B is a perspective view of the continuous soft work in the condition supplied to the sealing apparatus.
Figure 9:
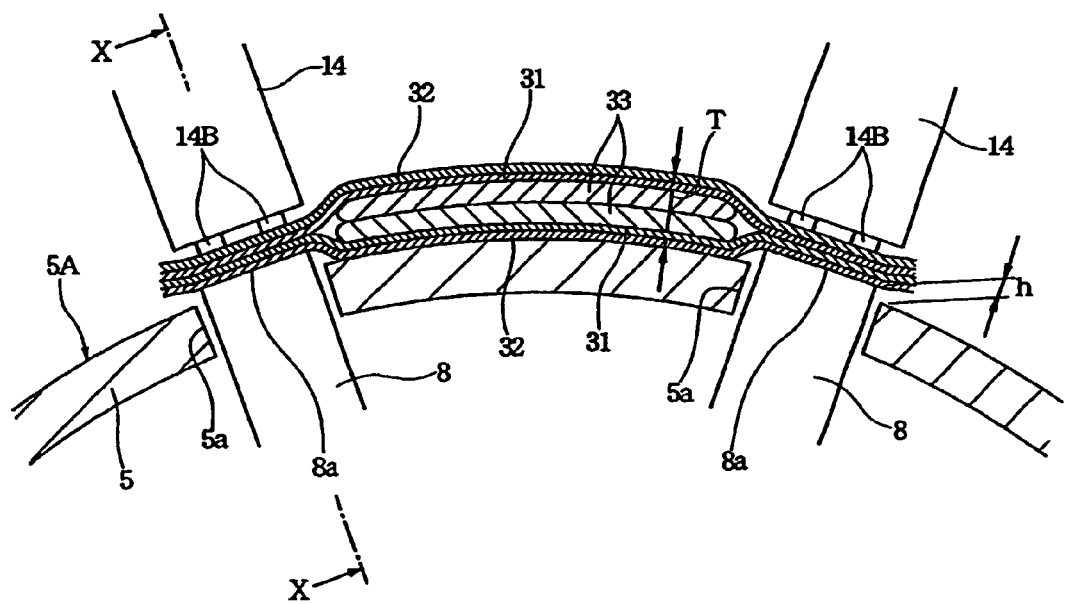
FIG. 9 is a section showing a condition where the continuous soft work is clamped between the horn and the anvil, where the section of the soft work is taken along line IX—IX of FIG. 8B.

In the developed, strip form body of FIG. 8A, a first sheet 32 is positioned at the back, and a second sheet 31 is stacked on the first sheet 32. The first sheet 32 has a larger width dimension than that of the second sheet 31. On one side 30A shown in FIG. 8A, the first sheet 32 is folded back to have its side edge 32a over the second sheet 31. Similarly, on the other side 30B, the first sheet 32 is folded back to have its side edge 32b over the second sheet 31. Such folded condition is shown in FIG. 10.

Figure 10:
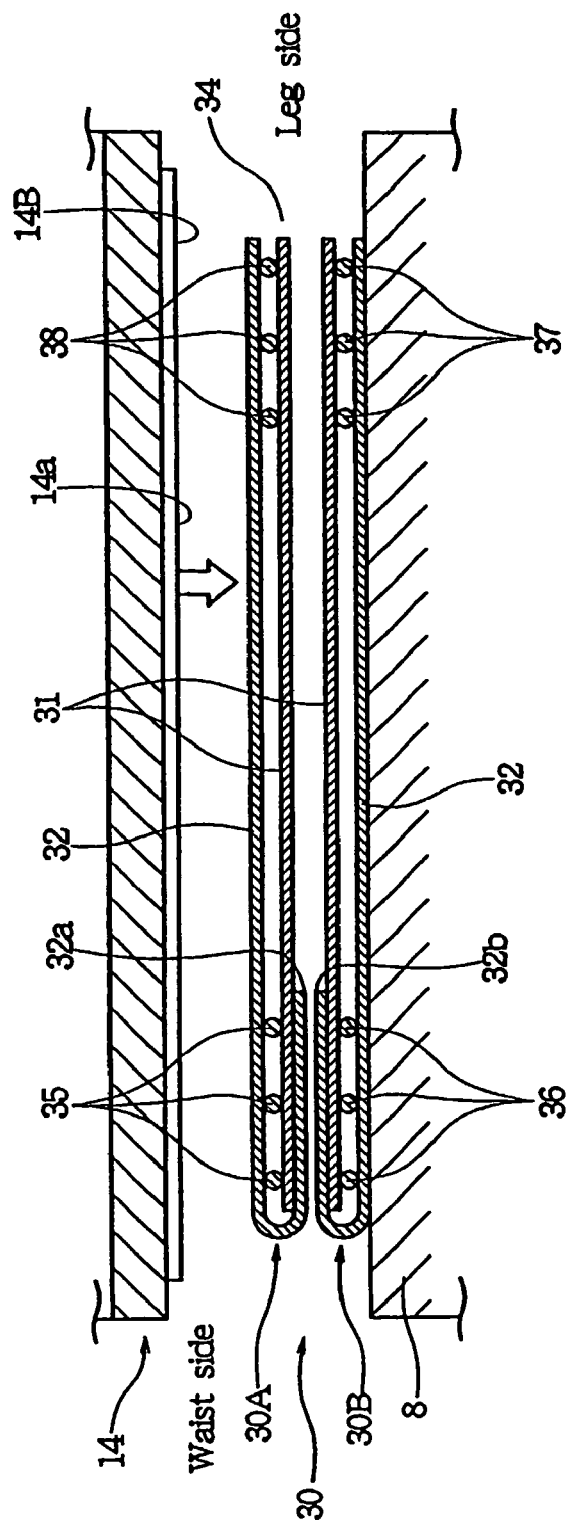
FIG. 10 is a section showing a condition where the continuous soft work is clamped between the horn and the anvil, where the section of the soft work is taken along line X—X of FIG. 8B.

As shown in FIG. 10, on one side 30A of the strip form body, a plurality of waist bands 35 are disposed between the first sheet 32 and the second sheet 31. On the other hand, on the other side 30B of the strip form body, a plurality of waist bands 36 are disposed between the first sheet 32 and the second sheet 31. The plurality of waist bands 35 and 36 are arranged in parallel relationship and extend straight in feeding direction of the strip form body.

Furthermore, between the first sheet 32 and the second sheet 31, leg bands 37 and 38 are provided. In the shown embodiment, respectively plurality of leg bands 37 and 38 are provided. The leg bands 37 and 38 are curved into waveform and extend in feeding direction of the strip form body, respectively. As shown in FIG. 8A, in regions surrounded by the leg bands 37 and 38, there are formed leg holes 34, which will serve as leg inserting portions of pants.

The waist bands 35 and 36 and the leg bands 37 and 38 are sandwiched between the first sheet 32 and the second sheet 31 in a condition elongated in feeding direction of the strip form body by a predetermined degree of elongation. Then, the first sheet 32, the second sheet 31, and the waist bands 35 and 36 and the leg bands 37 and 28 sandwiched there between are bonded with each other by hot-melt type adhesive or the like.

The first sheet 32 and the second sheet 31 has air permeability and liquid blocking ability and are heat-fusible. For instance, the first sheet 32 and the second sheet 31 may be spun bonded or melt blown non-woven fabric formed from thermoplastic synthetic fibers, or a laminated sheet of the foregoing non-woven fabrics. In an alternative, one of the first sheet 32 and the second sheet 31 may be the non-woven fabric and the other may be air permeable plastic film.

The waist bands 35 and 36 and the leg bands 37 and 38 are formed from elastically extensible member, such as string form or band form rubber or synthetic rubber.

On the surface of the second sheet 31, liquid absorptive bodies 33 are provided between adjacent leg holes 34. The liquid absorptive bodies 33 are of hourglass shape or rectangular shape and are arranged with a given interval along feeding direction of the strip form body. The liquid absorptive body may be formed by wrapping crushed pulp, mixture of crushed pulp and super absorbent polymer (SAP), a laminate of hydrophilic non-woven fabrics, air-laid pulp, or the like, in a liquid permeable top sheet. Then, the respective liquid absorptive bodies 33 are bonded on the surface of the second sheet 31 by hot-melt type adhesive or the like.

The top sheet may be formed from spunlaced non-woven fabric, through-air bonded non-woven fabric, plastic film having apertures for liquid passage, or the like.

The continuous soft work 30 shown in FIG. 8B is formed by folding the strip form body shown in FIG. 8A along a longitudinally extending center line O1—O1 into two ply sheet. When the soft work 30 is supplied to the sealing apparatus 1, the soft work 30 in which the first sheet 32 and the second sheet 31 are stacked, is clamped between the horn 8 and the anvil 14 at a position between adjacent liquid absorptive bodies 33 for ultrasonic sealing. As shown in FIG. 10, the soft work 30 to be clamped between the horn 8 and the anvil 14 has the smallest thickness in the intermediate portion where four sheets (two first sheets 32 and two second sheets 31) are stacked.

On the other hand, the soft work 30 has the largest thickness in the portion to be the waist side of pants where the folded-back portions of the first sheet 32 having the side edges 32a and 32b are further stacked in addition to the four sheets and the waist bands 35 and 36 are disposed therein. In the portion to be the leg side of pants close to the leg holes 34, the leg bands 37 and 38 are disposed in stacked four sheets. Therefore, the thickness of the leg side is greater than that of the intermediate portion and smaller than that of the waist side.

Since the first sheet 32 and the second sheet 31 are formed from a heat-fusible material, they generate an internal heat due to vibration applied from the horn. Thus, the first sheet 32 and the second sheet 31 are welded depending upon fine projection pattern formed on the seal opposing surfaces 14a of the anvil 14 to form the sealed portion S.

In the example of FIG. 8B, a pattern of the sealed portion S formed by the fine projection pattern is such that thin seal lines are repeated in a row. After formation of the sealed portions S by the sealing apparatus 1, the continuous soft work 30 is cut along the cutting lines C1—C1 between adjacent sealed portions S to complete pants type disposable diapers as soft absorbent articles.

It should be noted that the soft absorbent article manufactured by the sealing apparatus according to the present invention may be sanitary napkin, panty liner and so forth.

Hereinafter, operation of the sealing apparatus 1 will be discussed.

As shown in FIG. 2, the continuous soft work 30 is wound on a supply roll 21 provided at a supply portion (i) and supplied to an outer peripheral face 5A of the rotary drum 5. The continuous soft work 30 is wrapped on the outer peripheral face 5A of the rotary drum 5 (in further detail on the seal opposing surfaces 8a of the horns 8 projecting from the outer peripheral face 5A) over an angle of about 180°, and is released from the rotary drum 5 at an eject portion (ii) to be externally withdrawn by wrapping on an eject roll 22.

The continuous soft work 30 is continuously fed to the supply portion (i) at a constant speed. In the sealing apparatus 1, a rotary driving force is transmitted to the timing wheel 2 to rotate the rotary shaft 3a, the rotary base 6 as rotating portion and the rotary drum 5 in counterclockwise direction in FIGS. 2 and 3 at a constant angular velocity.

Here, the continuous soft work 30 contact with the seal opposing surfaces 8a of the horns 8 projecting from the outer peripheral face 5A of the rotary drum 5 thus rotating. Therefore, in the shown embodiment, the angular velocity of the rotating portion is set so that the rotational peripheral speed of the seal opposing surfaces 8a matches with the supply speed of the continuous soft work 30. Accordingly, on the outer peripheral face 5A of the rotary drum 5, the seal opposing surfaces 8a of the horns 8 and the continuous soft work 30 rotate together without causing any slippage with respect to each other.

The circumferential arrangement pitch of the horns 8 projecting from the outer peripheral face 5A of the rotary drum 5 matches with the arrangement pitch of the liquid absorptive bodies 33 and the arrangement pitch of the leg holes 34 of the continuous soft work 30 shown in FIG. 8B. Therefore, when the continuous soft work 30 is supplied to the outer peripheral face 5A of the rotary drum 5, the liquid absorptive body 33 is located between adjacent horns 8 (between adjacent sealing mechanisms) as shown in FIG. 9, so that the seal opposing surface 8a of the horn 8 confronts the portion where the liquid absorptive body 33 is not present.

While the rotary base 6 and the rotary drum 5 are rotated in counterclockwise direction at constant speed, the follower 10a provided in the rocking portion 10 of the rocking support member 9 moves along the cam groove 15c of the cam member 15 provided on the stationary table 4.

As shown in FIGS. 3 and 5, when the follower 10a is moved from the angular position A0 to the angular position A1 in the cam groove 15c by rotation of the rotary base 6, the follower 10a is moved to approach to the rotation center axis O—O by the cam groove 15c. As shown in lower portion of FIG. 1 and FIG. 6, therefore, while the follower is moved from the angular position A0 to the angular position A1, the rocking support member 9 is pivoted radially outwardly about the rocking shaft 10A, so that the anvil 14 held in the rocking support member 9 is oriented outwardly at an angle substantially 90° with respect to the rotation center axis O—O. It should be noted that at this time, the rocking support member 9 is pivoted within the cut-out portion 15a of the cam member 15. Therefore, the rocking support member 9 can be pivoted up to the position where the seal opposing surface 14a of the anvil 14 is placed at 90° with respect to the rotation center axis O—O.

The supply portion (i) and the eject portion (ii) for supplying and ejecting the continuous soft work 30 are located between the angular position A0 and the angular position A1. Between these angular positions, the anvil 14 is pivoted to the retracted position so as not to interfere with the continuous soft work 30, away from the path of the continuous soft work 30 to be supplied to the rotary drum 5 and the path of the continuous soft work 30 ejected from the rotary drum 5. Accordingly, supplying and ejecting of the continuous soft work 30 will never be interfered by the anvil 14.

When the follower 10a is moved from the angular position A1 and the angular position A2, the follower 10a is moved toward outer periphery as guided by the cam groove 15c. Therefore, the rocking support member 9 is pivoted toward the outer peripheral face 5A of the rotary drum 5. When the follower 10a moved across the angular position A2, then, in a region of the continuous soft work 30 where the liquid absorptive body 33 is not provided, the stacked body of the first sheet 32, the second sheet 31, the waist bands 35 and 36 and the leg bands 37 and 38 (see FIG. 10) is clamped by the seal opposing surface 8a of the horn 8 and the seal opposing surface 14a of the anvil 14, as shown in FIG. 9. Then, this condition is maintained up to a position short of the angular position A3.

Furthermore, while the follower 10a is moved from the angular position A3 to the angular position A0, the follower 10a is guided by the cam groove 15c toward the rotation center axis O—O, so that the anvil 14 is pivoted away from the horn 8 and the continuous soft work 30. Then, when the follower 10a reaches the angular position A0, the anvil 14 is pivoted to the retracted position angled at about 90° with respect to the rotation center axis O—O, as shown in FIG. 6.

While the follower 10a of each rocking support member 9 is moved from the angular position A2 to the angular position A3, electric power is supplied to the ultrasonic generating means 7 for a predetermined period to drive the horn 8 to vibrate for the predetermined period for forming the sealed portions S in the continuous soft work 30, as shown in FIG. 8B. At these sealed portions S, the soft work 30 is fusion-bonded. Then, the continuous soft work 30 after completion of seal as shown in FIG. 8B is ejected by the eject roll 22. The continuous soft work 30 ejected by the eject roll 22 is cut along the cutting line C1—C1 shown in FIG. 8B between adjacent sealed portions S to product individual pants type diapers.

FIG. 6 shows a condition where the rocking support member 9 is pivoted to the retracted position. At this condition, the seal opposing surface 8a at the leading end of the horn 8 matches with a plane Lh parallel to the rotation center axis O—O and to the outer peripheral face 5A of the rotary drum 5. The rocking center of the rocking support member 9 (center of the rocking shaft 10A) is located on the plane Lh. In FIG. 6, a plane extending across the rocking center and perpendicular to the plane Lh is indicated at Lv. In the condition of FIG. 6, the mounting surface 11B of the holding portion 11 of the rocking support member 9 is parallel to the plane Lv.

In the condition of FIG. 6, the seal opposing surface 14a of the anvil 14 pivoted to the retracted position is slightly projected toward the horn 8 beyond the plane Lv. The projecting amount is compression margin of the elastic member 13 when the anvil 14 is pressed onto the horn 8 as reached in clamping position.

Air supply to the elastic member 13 via the nozzle 13b is controlled to provide a predetermined internal pressure. In the condition shown in FIG. 6, the supporting plate 13A of the elastic member 13 is urged onto the tilted inner surfaces 11c of the frame portions 11a of the holding portion 11 by the internal pressure of the elastic member 13. Therefore, the seal opposing surface 14a of the anvil 14 is tilted at the tilting angle θ with respect to the plane Lv to increase projecting amount from the plane Lv as increasing distance from the rocking shaft 10A.

While the follower 10a is moved from the angular position A1 to the angular position A2 as shown in FIGS. 3 and 5, the rocking support member 9 is pivoted toward the outer peripheral face 5A of the rotary drum 5. At the final stage of the pivoting operation, the seal opposing surface 14a of the anvil 14 abuts onto the seal opposing surface 8a of the horn 8 with clamping the continuous soft work 30 as shown in FIG. 7A.

Here, in FIG. 6, the seal opposing surface 14a of the anvil 14 is tilted toward contacting direction with the horn 8 as increasing distance from the rocking center. Therefore, as shown in FIG. 7A, when the rocking support member 9 is pivoted over an angle (90°-θ) from the condition of FIG. 6, the seal opposing surface 14a of the anvil 14 is placed substantially parallel to the seal opposing surface 8a of the horn 8.

Then, when the following 10a reaches the angular position A2 and the rocking support member 9 is pivoted over 90° from the plane Lv as shown in FIG. 7B, the surface of the supporting plate 13A of the elastic member 13 is placed away from the inner surfaces 11c of the frame portions 11a of the holding portion 11. Then, the mounting surface 11B, the supporting plate 13A and the seal opposing surface 14a are placed in parallel or substantially parallel relationship with each other. The anvil 14 is subject to elastic force of the elastic member 13 to be elastically pressed toward the horn 8.

As set forth above, since the seal opposing surface 14a of the anvil 14 is projected from the plane Lv with the tilting angle θ in the condition shown in FIG. 6, the seal opposing surface 8a of the horn 8 and the seal opposing surface 14a of the anvil 14 come into contact with each other in parallel or substantially parallel relationship in the condition shown in FIG. 7A. Subsequently, elastic pressure from the elastic member 13 acts on the anvil 14. Accordingly, when the anvil 14 is urged onto the horn 8 under pressure by pivoting motion, displacement motion of the seal opposing surface 14a of the anvil 14 relative to the sealing opposing surface 8a of the horn 8 along the plane Lh is hardly caused.

This is because, when the seal opposing surface 14a of the anvil 14 and the seal opposing surface 8a of the horn 8 begin to contact, these surfaces contact as parallel surfaces. In addition, the seal opposing surfaces 8a and 14a are hardly damaged. Moreover, since the clamping of the continuous soft work 30 is performed by parallel surfaces, the continuous soft work 30 can be certainly clamped between the seal opposing surface 8a and the seal opposing surface 14a.

On the other hand, when the continuous soft work 30 is the continuous body of the pants type disposable diapers, the continuous soft work 30 is not flat in the portion where the sealed portion S is to be formed with the horn 8 and the anvil 14, as shown in FIG. 10. Namely, the thickness is the largest in the waist side, decreased in the intermediate portion, and then increased in the leg side. Accordingly, the soft work 30 to be sealed is locally different in thickness and has unevenness on the surface.

As set forth above, although the portion forming the sealed portion S does not have uniform thickness and varies in thickness over different portions thereof, because the anvil 14 is urged toward the horn 8 by an air dumper i.e., the bag shaped elastic body filled with air (fluid), the seal opposing surface 14a of the anvil 14 can flexibly follow to variation of the thickness of the continuous soft work 30. Furthermore, by the internal pressure of the elastic body 13, the continuous soft work 30 can be substantially uniformly depressed at respective portions of the sealed portion S by the horn 8 and the anvil 14. Thus, seal quality of the sealed portion S can be made uniform.

On the other hand, the internal pressure inside of the bag body of the elastic member 13 can be controlled by supply of air pressure through the nozzle 13b. Therefore, control for varying the internal pressure inside of the bag body of the elastic member 13 is facilitated depending upon the material and structure of the continuous soft work 30 to be sealed. Accordingly, even when the structure of the continuous soft work 30 is varied and associating therewith, the seal pattern on the seal opposing surface 14a of the anvil 14 is varied, preparation can be completed merely by changing the internal pressure of the elastic member 13 to permit sealing operation under optimal condition, constantly.

Furthermore, in the sealing mechanism of this embodiment, since mechanism to perform sealing after clamping the continuous soft work 30 is employed, sealing condition can be constantly maintained at any production speed by setting power supply period to the ultrasonic generating means 7 at a given period and by setting the sealing pressure at a predetermined magnitude. Thus, various production speeds can be realized.

Also, it is preferred to mount the ultrasonic generating means 7 in movable manner along normal direction (radial direction) with respect to the rotary drum 5 so that the projection height h of the leading end of the horn 8 from the outer peripheral face 5A of the rotary drum 5 can be varied. By taking such construction, the projection height h can be varied depending upon the thickness of the liquid absorptive body 33 of the soft work 30 to certainly seal the sheets for any product provided with the liquid absorptive body.

On the other hand, when the continuous soft work 30 is formed by folding even the liquid absorptive bodies 33 together with respective sheets, as shown in FIG. 8B, the projection height h shown in FIG. 9 is preferably one half of the thickness T of the continuous soft work 30 at the portion where the liquid absorptive body 33 is provided. Namely, it is preferred that the projection height h is substantially equal to the thickness of the liquid absorptive body 33 in developed condition.

By setting as set forth above, in the portion where the liquid absorptive body 33 is not provided, the sheets 31 and 32 can be certainly clamped by the horn 8 and the anvil 14 without being influenced by the thickness of the liquid absorptive body 33.

In the shown embodiment, the horn 8 is fixed on the side of the rotation center axis O—O and the anvil 14 is provided rockably outwardly of the horn 8. However, conversely, it is also possible that the anvil 14 is fixed on the side of the rotation center axis O—O and the horn 8 is provided for rocking motion. On the other hand, the sealing mechanism may be a heat sealing mechanism for establishing seal by heating a first clamping member and a second clamping member and clamping the continuous soft work with these first and second clamping members.

In the first embodiment, on the other hand, the rocking driving means is formed from the follower 10a projecting from the rocking support member 9 and the cam groove 15c formed in the cam member 15. However, conversely, it is also possible that a projecting cam follower is formed in the cam member and a recess or groove to be guided along the projecting cam follower is formed in the rocking support member.

As the rocking driving means for driving the rocking support member 9, a cylinder mechanism or the like or a link mechanism which will be discussed later in discussion for the second embodiment may also be employed.

On the other hand, the elastic member 13 for biasing the anvil may be a coil spring or the like in place of the elastic member discussed above.

Figure 11:
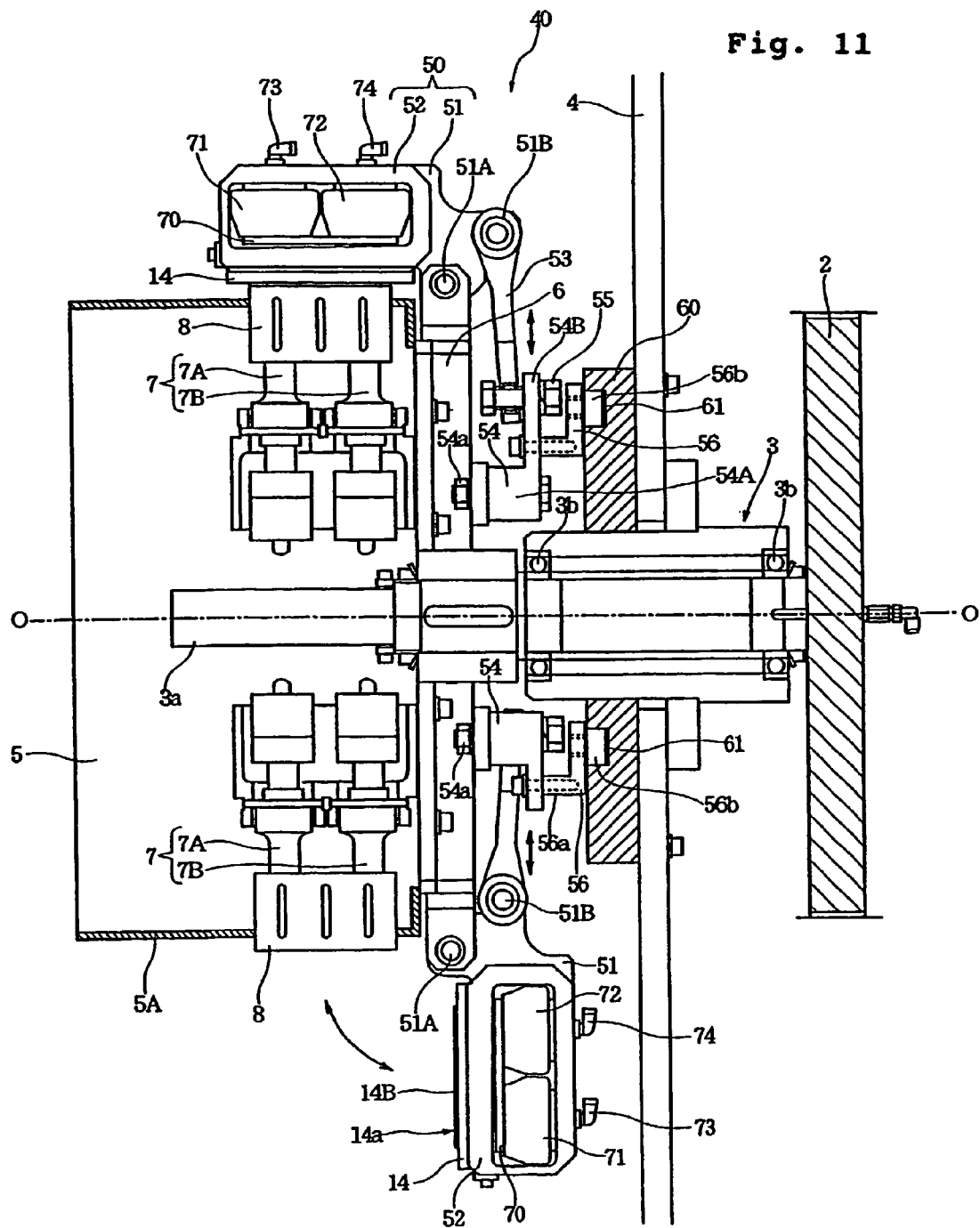
FIG. 11 is a vertical section of a sealing apparatus according to a second embodiment of the present invention.
Figure 12:
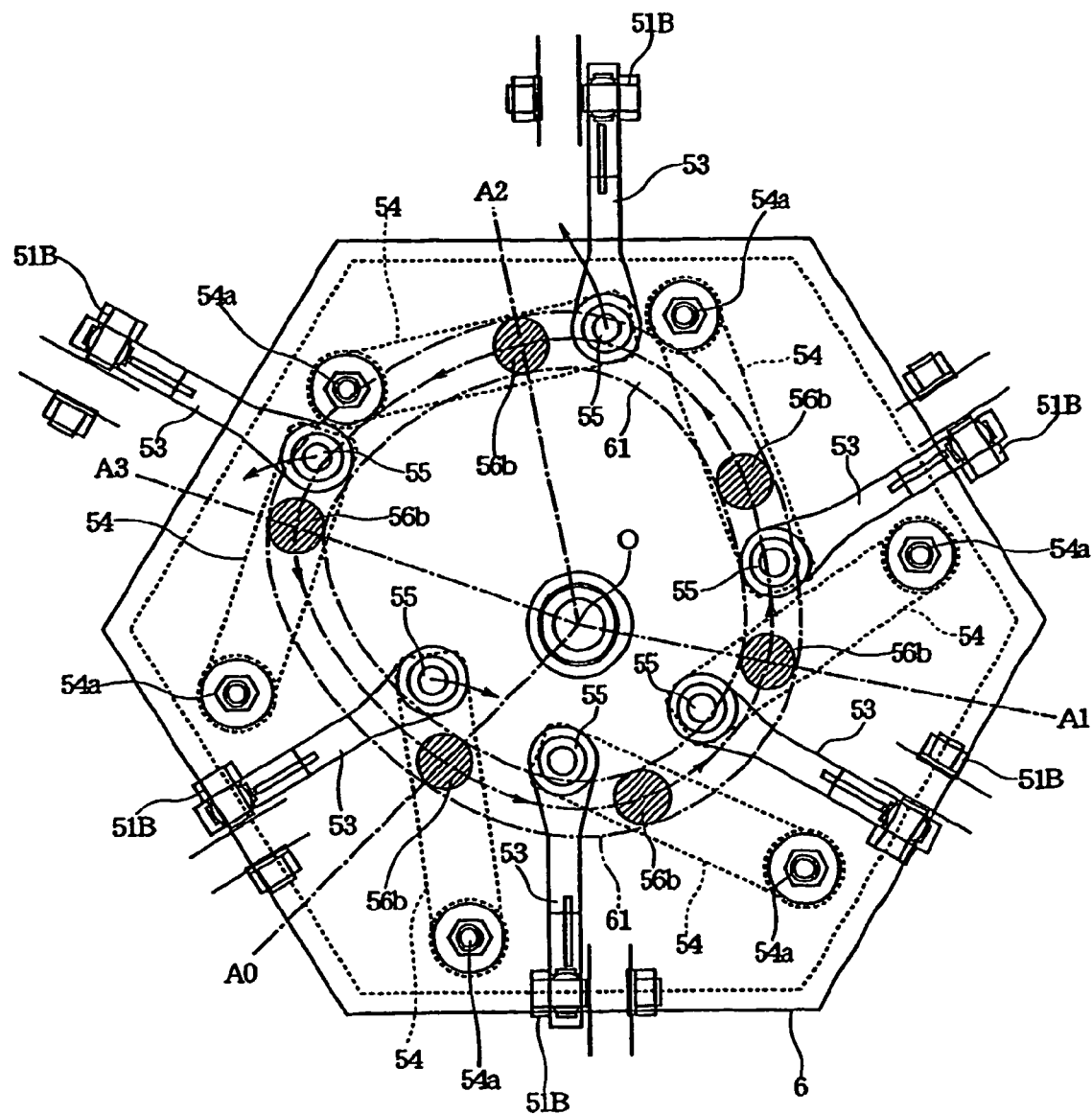
FIG. 12 is a front elevation showing a structure of a cam member.
Figure 13:
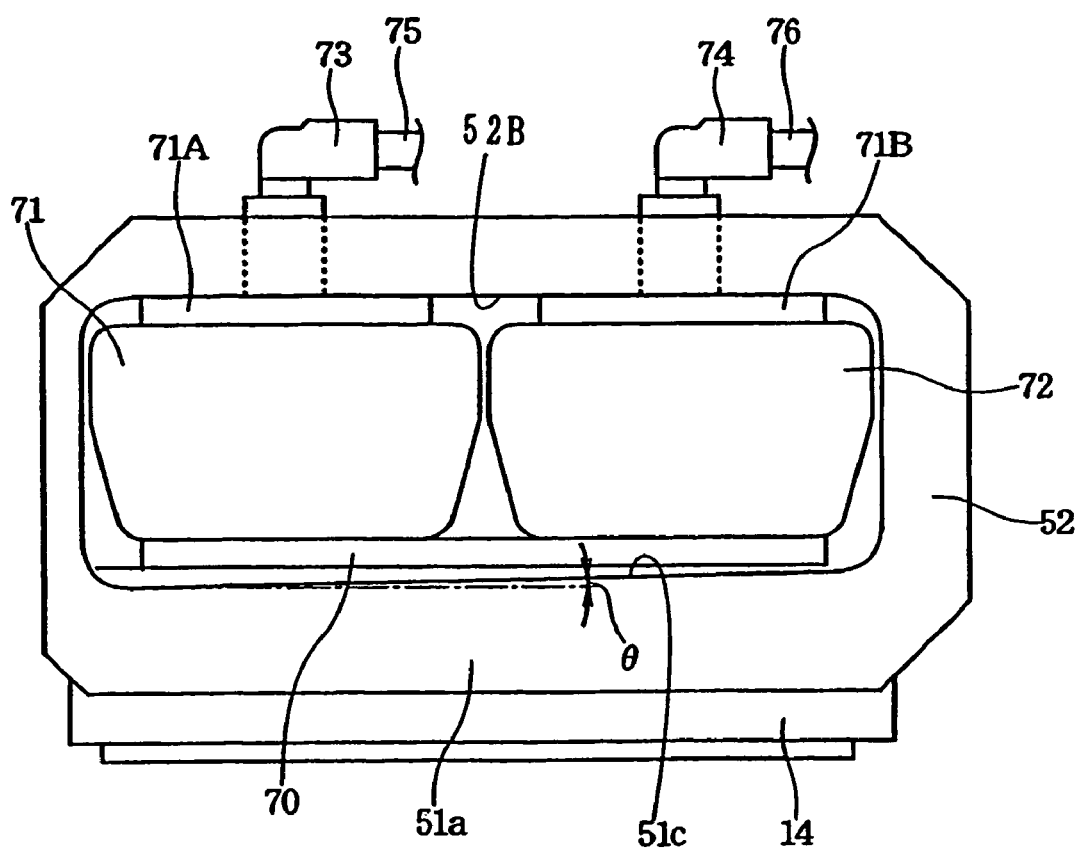
FIG. 13 is a side elevation of a rocking support portion.
Figure 14:
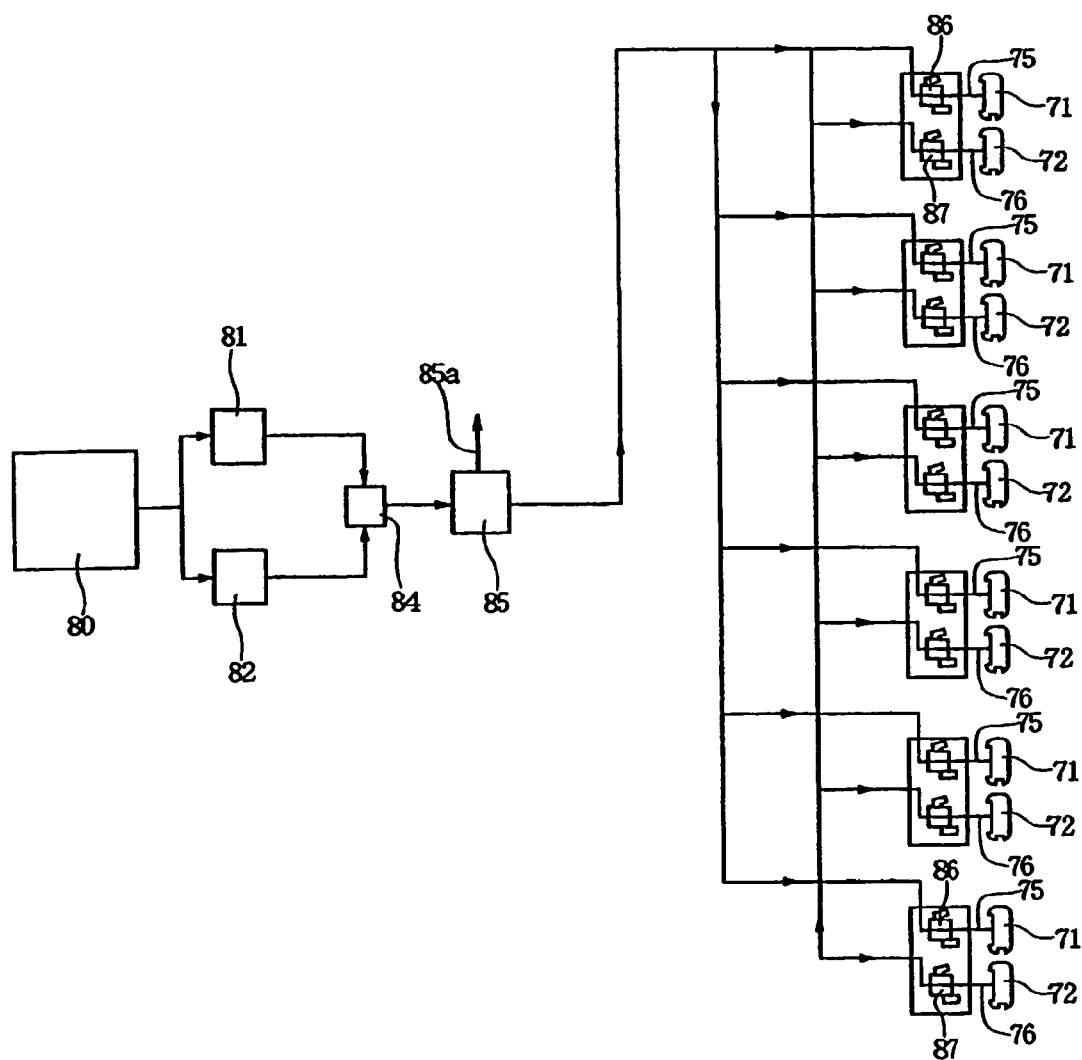
FIG. 14 is an explanatory illustration of a piping for supplying air to an elastic member.

FIGS. 11 to 14 show a sealing apparatus 40 according to a second embodiment of the present invention. FIG. 11 is a vertical section of the sealing apparatus 40, FIG. 12 is a front elevation showing a structure of a cam member, FIG. 13 is a side elevation showing a supporting condition of the anvil 14, and FIG. 14 is an illustration showing a construction of a piping for setting internal pressure of elastic members.

The sealing apparatus 40 shown in FIG. 11 is different from the sealing apparatus 1 of the first embodiment only in constructions of the rocking driving means and the ultrasonic generating means, number of the elastic members supporting each anvil 14, and an internal pressure setting condition for respective elastic members. Other constructions are substantially the same as the first embodiment.

Namely, the soft work 30 to be continuously supplied is similar to that shown in FIGS. 8A, 8B to 10. Seal timings A0, A1, A2 and A3 of the sealing mechanism are the same as those of the sealing apparatus 1. Furthermore, the position of the rotation center of the rocking support member, the tilting angle θ of the anvil 14 when the rocking support member is pivoted to the retracted position, relative motion of the anvil 14 and the horn 8 when the anvil 14 is pivoted to abut on the horn 8, the optimal value of the projecting height h of the horn 8 from the rotary drum 5 and so forth are the same as the sealing apparatus 1.

It should be noted that, in the following disclosure, like components to those of the sealing apparatus 1 of the first embodiment will be identified by like reference numerals and detailed discussion therefore will be eliminated for avoiding redundant discussion and whereby to keep the disclosure simple enough to facilitate clear understanding of the present invention.

The sealing mechanism in the sealing apparatus 40 shown in FIGS. 11 and 12, is an ultrasonic sealing apparatus comprising the horn 8 as the first clamping member and the anvil 14 as the second clamping member. Different from the first embodiment, the horn 8 is driven by a plurality of ultrasonic generating means 7 to vibrate. In the embodiment shown in FIG. 11, in each of sealing mechanisms radially arranged in the rotary drum 5, two ultrasonic generating means 7A and 7B are provided. Two ultrasonic generating devices 7A and 7B are arranged along the width direction of the rotary drum 5, namely the direction of the rotation center axis O—O of the rotary drum 5. When the horn 8 is driven by the ultrasonic generating means 7A and 7B thus arranged to vibrate, output of ultrasonic vibration to be applied to the soft work 30 from the horn 8 can be enhanced.

As shown in FIG. 10, in the portion forming the sealed portion S of the soft work 30, the thickness of the stacked body is large in the waist side and the leg side. Accordingly, by arranging two ultrasonic generating devices 7A and 7B along the rotation center axis O—O, ultrasonic vibration can effectively act on the thick portions of the soft work 30 for uniformly fusion-bonding overall seal region of the soft work 30.

It should be noted that, in each sealing mechanism, ultrasonic vibration is applied to the common horn 8 by two ultrasonic generating means 7A and 7B in the shown embodiment. However, it is also possible to provide two horns and to support respective horns by respective ultrasonic generating means 7A and 7B.

The rotary drum 5 is fixed on the rotary base 6 of equilateral hexagonal front elevation as shown in FIG. 12. At the center portion of each edge of the equilateral hexagonal shape of the rotary base 6, the rocking support member 50 is supported. Accordingly, the rocking support members 50 are spaced 60° from each other. The rocking support member 50 is constructed to include a rocking portion 51 and a holding portion 52. The rocking portion 51 and the holding portion 52 are fixed with each other. Each rocking portion 51 is rockably supported on the edge of the rotary base 6 by a rocking shaft 51A. It should be noted that the rocking shaft 51A is oriented perpendicular to the rotation center axis O—O.

On the surface of the stationary table 4 opposing to the rotary base 6, a cam member 60 forming the rocking driving means is secured. The cam member 60 is of flat plate shape having a predetermined thickness, and is formed with a cam groove 61 to be a cam profile on the front surface. The cam groove 61 is continuous around the rotation center axis O—O. A depth direction of recessed portion of the cam groove 61 is oriented in parallel to the rotation center axis O—O.

As shown in FIG. 11, a link mechanism is provided between the rocking portion 51 and the cam member 60. In the link mechanism, a drive link 53 is pivotably supported on the rocking portion 51 through a connection shaft 51B provided in an orientation perpendicular to the rotation center axis O—O.

On the back surface of the rotary base 6, a base portion 54A of a pivotal link 54 is pivotably supported by a support shaft 54a. The axial direction of the support shaft 54a is parallel to the rotation center axis O—O. The leading end of the drive link 53 is pivotably connected to the leading end portion of an arm portion 54B of the pivotal link 54 through a connection shaft 55. The axial direction of the connection shaft 55 is parallel to the rotation center axis O—O.

On the pivotal link 54, the driving member 56 is mounted. The driving member 56 includes a driving support body 56a fixed at the intermediate portion of the pivotal link 54 in non-pivotable fashion, and a follower 56b provided on the driving support body 56a. The follower 56b is movable along the cam groove 61. The follower 56a may roll or slide without rolling along the cam groove 61.

In FIG. 12, the driving support body 56a is eliminated for the purpose of illustration, showing relative position between the pivotal link 54, the follower 56b and the drive link 53.

When the rotary base 6 is rotated, the follower 56b moves along the cam groove 61. At this time, a distance between the follower 56b and rotation center axis O—O is varied depending upon shape of the cam groove 61. Depending on this variation, the pivotal link 54 is pivoted, and then, the rocking support member 50 is pivoted through the drive link 53. In the shown embodiment, the rocking driving means is formed from the cam member 60 and the follower 56b.

Thus, the rocking support member 50 is pivoted by the cam groove 61. Pivoting timing of the rocking support member 50 is the same as the sealing apparatus 1 of the first embodiment. When the follower 56b is moved from the angular position A2 to the angular position A3, the rocking support member 50 is pivoted about the rocking shaft 51A toward the outer peripheral face 5A of the rotary drum 5 to reach the clamping position. On the other hand, while the follower 56b is moved from the angular position A0 to the angular position A1, the rocking support member 50 is pivoted about the rocking shaft 51A toward the stationary table 4 over about 90° to be placed at the retracted position.

As shown in FIGS. 11 and 13, in the second embodiment, two elastic members 71 and 72 are provided in each holding portion 52. Two elastic members 71 and 72 are arranged along the width direction of the rotary drum 5, namely along the rotation center axis O—O.

The elastic members 71 and 72 are similar to the elastic member 13 shown in FIG. 4. That is, each of the elastic members 71 and 72 comprises an elastically deformable bag body, in which air as fluid is supplied.

The basic construction of the holding portion 52 is the same as the holding portion 11 shown in FIG. 4. Two elastic members 71 and 72 are fixed on a mounting surface 52B of the holding portion 52 via fixing plates 71A and 71B. At positions opposing to the mounting surface 52B, the holding portion 52 also has frame portions 51a and 51a similar to the frame portions 11a and 11a of FIG. 4. The frame portions 51a and 51a has inner surfaces 51c and 51c, which are tilted at the angle θ with respect to the plane parallel to the mounting surface 52B to approach toward the horn 8 as increasing distance from the rocking shaft 51A.

On the other ends of the elastic members 71 and 72, a supporting plate 70 is secured. On the supporting plate 70, the anvil 14 is secured. In the condition where the anvil 14 is not in contact with the horn 8, the supporting plate 70 is urged onto the inner surfaces 51c and 51c by fluid pressure within the elastic members 71 and 72. As a result, the surface of the anvil 14 has the tilting angle θ. Effect of providing the tilting angle θ is the same as the sealing apparatus 1 of the first embodiment.

On the fixing plates 71A and 71B, nozzles 73 and 74 are provided. To these nozzles 73 and 74, air pipes 75 and 76 are connected. Through the air pipes 75 and 76 and the nozzles 73 and 74, the internal pressures in the elastic members 71 and 72 can be set individually.

As shown in FIG. 10, in the seal region of the soft work 30 to be clamped by the horn 8 and the anvil 14, the thickness in the waist side is greater than the thickness in the leg side. Accordingly, in the shown embodiment, the internal pressure of the elastic member 72 urging the anvil 14 at the leg side is set to be slightly higher than the internal pressure of the elastic member 71 urging the anvil at the waist side.

As a result, the anvil 14 is urged onto the horn 8 with relatively large pressure on the leg side, and the anvil 14 is urged onto the horn 8 with relatively small pressure on the waist side. As a result, the soft work 30 having different thicknesses can be substantially uniformly fusion-bonded over entire length from the waist side to the leg side. Thus, local excessive fusing can be avoided which might otherwise cause locally stiffening of the sealed portion S to degrade texture in final absorbent articles.

Also, since uniform seal can be formed over the portions having mutually different thicknesses, failure of sealing is hardly caused even when the internal pressures of both of the elastic members 71 and 72 are not excessively large. Therefore, it can be avoided to apply excessive pressure on the soft work and whereby to avoid fusion of the sheet.

Individually setting of the internal pressures in the plurality of elastic members 71 and 72 is effective in the case where the soft work 30 has portions mutually different in thickness, as set forth above. However, it is also effective is the case where different materials are distributed in the portion to be sealed, in place of or in addition to the foregoing case. For example, when materials having different melting temperatures are distributed in different positions in the portion to be sealed, the internal pressure of the elastic member opposed to the material having high melting temperature is elevated; the internal pressure of the elastic member opposed to the material having low melting temperature is lowered. Thus, uniform sealed portion can be formed.

It should be noted that, in the shown embodiment, the anvil 14 is single. However, it is possible to separately provide two anvils: one to be biased by the elastic member 71; and the other to be biased by the elastic member 72. It is also possible to provide a single anvil having a thin portion formed between a portion supported by the elastic member 71 and a portion supported by the elastic member 72 for permitting independent behavior of the portion to be biased by the elastic member 71 and the portion to be biased by the elastic member 72.

FIG. 14 shows a piping to be pressure setting means, which can variably set the internal pressure of respective of the elastic members 71 and 72 respectively provided in each sealing mechanism.

A high pressure air is applied to two pressure setting portions 81 and 82 from an air pressure generating portion 80, such as air pump or the like. One pressure setting portion 81 is adapted to set supply pressure to the elastic members 71 and 72 at a predetermined value when sealing operation is performed for the soft work 30. The other pressure setting portion 82 is for discharging air from the elastic members 71 and 72 for releasing the pressure to the supporting plate 70 by the elastic members 71 and 72. This pressure setting portion 82 is used in set-up operations such as supplying of the soft work 30 to the sealing apparatus 40 and rotating of the rotary drum 5 for a predetermined period upon initiation of sealing operation, for example. The pressure setting portions 81 and 82 may be constructed as regulators employing diaphragms.

The pressure setting portions 81 and 82 are switched by a switching valve 84. Forward of the switching valve 84, there is provided a pressure sensor 85. The pressure sensor 85 is designed to generate an electric signal 85a when the pressure within the piping is lowered across a predetermined value. When the electric signal 85a is generated, sealing operation by the sealing apparatus 40 is interrupted.

In each sealing mechanism, a pressure reducing pressure control valve 86 communicated with inside of the elastic member 71 through a pipe 75 and a pressure reducing pressure control valve 87 communicated with inside of the elastic member 72 through a pipe 76 are provided. During sealing operation, the pressure set by the pressure setting portion 81 is reduced by the pressure reducing pressure control valve 86 to be supplied to the elastic member 71 and is reduced by the pressure reducing pressure control valve 87 to be supplied to the elastic member 72.

The pressure reducing pressure control valves 86 and 87 can individually set pressures to be supplied to the elastic members 71 and 72 by adjusting an amount of valve opening. By this, as set forth above, the internal pressure of the elastic member 71 is set slightly low and the internal pressure of the elastic member 72 is set slightly high, for example.

Here, it is also possible to provide only two pressure reducing pressure control valves in the sealing apparatus 40: one pressure reducing pressure control valve being for simultaneously adjusting all of air pressures to be supplied to the plurality of elastic members 71; and the other pressure reducing pressure control valve being for simultaneously adjusting all of air pressures to be supplied to the plurality of elastic members 72.

Among piping shown in FIG. 14, the pressure sensor 85 and the pressure reducing pressure control valves 86 and 87 are mounted on the rotary base 6, and piping connecting the switching valve 84 and the pressure sensor 85 is arranged along the rotation center axis O—O, and is extended externally from the sealing apparatus 40 via a rotary joint.

It should be noted that even in the sealing apparatus 1 of the first embodiment, similar piping as that shown in FIG. 14 is provided. However, in case of the sealing apparatus 1, a single pressure reducing pressure control valve is provided for each sealing mechanism.

In the first embodiment, the construction, in which a single elastic member 13 is provided in each holding portion 11, has been disclosed. In the second embodiment, on the other hand, the construction, in which two elastic members 71 and 72 are provided in each holding portion 52, has been disclosed. However, the present invention is not limited to these embodiments, and three or more elastic members may be provided for each holding portion.

As a result of the various structures described in detail above, advantages of the present invention may include one or more of the following:

(1) Sealed portions can be formed in predetermined positions of a continuous soft work at high speed;

(2) Clamping and unclamping of the continuous soft work by a first clamping member and a second clamping member of sealing mechanism can be performed quickly and certainly; and (3) Since the clamping and unclamping can be performed only by rocking or pivoting motion of the second clamping member, operation of the apparatus can be simplified and construction of the apparatus can be simplified.

Particularly, if the second clamping member is pivoted by the use of a cam member, as in the foregoing embodiments, rotating force of a rotating portion can be used for driving the second clamping member in clamping and unclamping directions. Therefore, the driving power source can be minimized.

On the other hand, if an elastic member having a casing, into which fluid is to be supplied, is employed for pressing the second clamping member, as in the foregoing embodiments, uniform pressure can be easily applied to the soft work by the second clamping member. In this case, additionally, since internal pressure of the elastic member can be freely set, initial setting can be changed only by varying the internal pressure even if the structure of the soft work is varied, to thereby improve work efficiency. Particularly, if a plurality of elastic members are provided in each sealing mechanism, uniform clamping force can be easily applied to a soft work having locally different thicknesses.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

The invention claimed is:

1. A sealing apparatus comprising:
   a sealing mechanisn, having a first clamping member and a second clamping member for clamping a fusion-bondable soft work therebetween to form sealed portions in said soft work; and
   driving means for driving a support member to make said second clamping member alternate between a clamping position closer to said first clamping member and a refracted position away from said first clamping member,
   wherein said second clamping member is supported on an elastic member provided in said support member, said elastic member having a deformable casing into which fluid is introduced, so that said second clamping member in said clamping position is biased toward said first clamping member by said elastic member while being allowed to tilt in accordance with a variation of thickness of said soft work
   wherein said support member has frame portions whose inner surfaces face said elastic member, wherein when said second clamping member is in said retracted position, said elastic member is restricted by said inner surfaces of said frame portions, whereas when said second clamping member is in said clamping position, said elastic member is free from said inner surfaces of said frame portions.

2. A sealing apparatus as set forth in claim 1, wherein said sealing mechanism is an ultrasonic sealing device, and one of said first clamping member and said. second clamping member is a horn and the other is an anvil.

3. A sealing apparatus as set forth in claim 1, wherein a plurality of sealing mechanisms are arranged to effect sealing at intervals.

4. A sealing apparatus as set forth in claim 1, wherein said soft work includes a fusion-bondable sheet and liquid absorptive bodies spaced apart from each other in a feeding direction thereof and supported by said sheet.

5. A sealing apparatus as set forth in claim 1, wherein said plurality of elastic members are provided in said support member to support said second clamping member.

6. A sealing apparatus as set forth in claim 5, further comprising:
   pressure setting means for individually setting internal fluid pressures of said elastic members.

7. A sealing apparatus as set forth in claim 1, wherein
   the supporting member has a mounting surface for mounting the elastic member; the inner surfaces in the frame portions of the support member oppose the mounting surface and are configured to tilt at an angle with respect to the mounting surface.

8. A method for manufacturing soft articles with sealed portions, comprising:
   forming sealed portions in a continuous soft work by clamping said soft work between a first clamping member and a second clamping member constituting a sealing mechanism; and
   cutting said soft work before, simultaneously with or after the forming step,
   wherein a support member is driven to make said second clamping member alternate between a clamping position, closer to said first clamping member and a retracted position away from said first clamping member and said second clamping member is supported on an elastic member provided in said support member, said elastic member having a deformable casing into which fluid is introduced, so that said second clamping member in said clamping position is biased toward said first clamping member by said elastic member while being allowed to tilt in accordance with a variation of thickness of said soft work,
   wherein said support member has frame portions whose inner surfaces face said elastic member, wherein when said second clamping member is in said retracted position, said elastic member is restricted by said inner surfaces of said frame portions, whereas when said second clamping member is in said clamping position, said elastic member is free from said inner surfaces of said frame portions.

9. A manufacturing method as set forth in claim 8, wherein said sealing mechanism is an ultrasonic sealing device, and one of said first clamping member and said second clamping member is a horn and the other is an anvil.

10. A manufacturing method as set forth in claim 8, wherein a plurality of sealing mechanisms are arranged to effect sealing at intervals.

11. A manufacturing method as set forth in claim 8,
   wherein said continuous soft work includes a fusion-bondable sheet and liquid absorptive bodies spaced apart from each other in a feeding direction thereof and supported by said sheet, and sealing is effected at positions between adjacent liquid absorptive bodies in a condition where said sheet is folded back.

12. A manufacturing method as set forth in claim 8, wherein said plurality of elastic members are provided in said support member to support said second clamping member.

13. A manufacturing method as set forth in claim 12, wherein internal fluid pressures of said elastic members are set individually.

14. A manufacturing method as set forth in claim 8, wherein
   the supporting member has a mounting surface for mounting the elastic member; the inner surfaces in the frame portions of the support member oppose the mounting surface and are configured to tilt at an angle with respect to the mounting surface.

* * * * *